US006392017B1

(12) United States Patent
Chandrashekar

(10) Patent No.: US 6,392,017 B1
(45) Date of Patent: May 21, 2002

(54) PARASITIC HELMINTH DIAG2 PROTEINS AND USES THEREOF

(75) Inventor: Ramaswamy Chandrashekar, Fort Collins, CO (US)

(73) Assignee: Heska Corporation, Fort Collins, CO (US)

(*) Notice: Subject to any disclaimer, the term of this patent is extended or adjusted under 35 U.S.C. 154(b) by 0 days.

(21) Appl. No.: 09/635,025

(22) Filed: Aug. 4, 2000

Related U.S. Application Data

(62) Division of application No. 09/361,434, filed on Jul. 27, 1999, now Pat. No. 6,136,963.

(51) Int. Cl.$^7$ .......................... C07K 14/00; C07K 5/00; C07K 16/00; G01N 33/53; C12N 9/00; A61K 39/00; A61K 39/395; C07H 21/04

(52) U.S. Cl. .................... 530/350; 530/300; 530/387.1; 435/7.1; 435/183; 424/184.1; 424/130.1; 536/23.1

(58) Field of Search ................................. 530/300, 350; 536/23.1; 514/2–21, 1.11; 424/93.1–130.1

(56) References Cited

U.S. PATENT DOCUMENTS 4,842,999 A 6/1989 Fuller et al. .................. 435/7

FOREIGN PATENT DOCUMENTS

| AU | 8776729 | 2/1988 |
| WO | WO 92/13560 | 8/1992 |
| WO | WO 94/15593 | 7/1994 |
| WO | WO 95/32988 | 12/1995 |

OTHER PUBLICATIONS

Q18066, Swiss–Prot, Dec. 15, 1998.*
Abraham et al., *J. Parasitol.*, 1991, vol. 77(2), pp. 254–257.
Abraham et al., *J. Parasitol.*, 1990, vol. 76(4), pp. 523–528.
Abraham et al., *Experimental Parasitology.*, 1990, vol. 70, pp. 314–322.
Abraham et al., *J. Parasitol.*, 1998, vol. 74(2), pp. 275–282.
Amiri et al., *Molecular and Biochemical Parasitology*, 1998, vol. 28, pp. 113–120.
Bianco et al., *Molecular and Biochemical Parasitology*, 1990, vol. 39, pp. 203–212.
Blair et al., *Fifth International Congress of Parasitol.*, Aug. 1982, Toronto, Canada.
Chomczynski et al., *Analytical Biochemistry*, 1987, vol. 162, pp. 156–159.
Coleman et al., *The Journal of Infectious Diseases*. 1986, vol. 154(1), pp. 33–39.
Culpepper et al., *Molecular and Biochemical Parasitology*, 1992, vol. 54, pp. 51–62.
Dalton et al., *Molecular and Biochemical Parasitology*, 1989, vol. 35, pp. 161–166.
Davis et al., *Am. Soc. Trop. Med. Hyg.*, 1988, Abstract #404, p. 256.
Delves et al., *Parasitol.*, 1989, vol. 99, pp. 99–104.
Denham., *International Journal of Nuclear Medicine and Biology*, 1980, vol. 7, pp. 105–111.
Frank et al., *J. Parasitol.*, 1991, vol. 77(6), pp. 950–956.
Gamble et al., *Molecular and Biochemical Parasitology*, 1989, vol. 33, pp. 49–58.
Grieve et al., *The Journal of Immunology*, 1992, vol. 148(8), pp. 2511–2515.
Grieve, *Proc. Heartworm Symp.*, 1989, pp. 187–190.
Grieve et al., *Am. J. Trop. Med. Hyg.*, 1988, vol. 39(4), pp. 373–379.
Grieve et al., *Epidemiologic Reviews*, 1983, vol. 5, pp. 220–246.
Hewick et al., *The Journal of Biological Chemistry*, 1981, vol. 256(15), pp. 7990–7997.
Hortez et al., *The Journal of Biological Chemistry*, 1985, vol.260(12), pp. 7343–7348.
Ibrahim et al., *Parasitology*, 1989, vol. 99, pp. 89–97.
Jwo et al., *Am J. Trop. Med. Hyg.*, 1989, vol. 41(5), pp. 553–562.
Kassis et al., *The Journal of Immunology*, 1979, vol. 123(4), pp. 1659–1662.
Lackey et al., *Experimental Parasitology*, 1989, vol. 68, pp. 176–185.
Lal et al., *The Journal of Immunology*, 1988, vol. 140, pp. 2032–2038.
Maki et al., *Jounal of Helminthology*, 1986, vol. 60, pp. 31–37.
McKerrow et al., *Biochem. J.*, 1985 vol. 231, pp. 47–51.
McKerrow et al., *Experimental Parasitology*, 1982, vol. 53, pp. 249–254.
McReynolds et al., 38th Annual Meeting, Dec. 1989, *Am J. Trop. Med. Hyg.*, Abstract #233, pp. 173–174.
McReynolds et al., 38th Annual Meeting, Am J. Trop. Med. Hyg., Dec. 1989, Abstract #445, p. 295.
Mok et al., *Molecular and Biochemical Parasitology*, 1988, vol. 31, pp. 173–182.
Noble et al., *Parasitology: the Biology of Animal Parasites*, 1982, pp. 256–322.

(List continued on next page.)

*Primary Examiner*—Ardin H. Marschel
*Assistant Examiner*—Shubo Joe Zhou
(74) *Attorney, Agent, or Firm*—Heska Corporation

(57) ABSTRACT

The present invention relates to parasitic hemline DiAg2 proteins; to parasitic helminth DiAg2 nucleic acid molecules, including those that encode such DiAg2 proteins; to antibodies raised against such DiAg2 proteins; and to compounds that inhibit parasitic helminth DiAg2 activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

12 Claims, No Drawings

OTHER PUBLICATIONS

Parab et al., *Immunology*, 1988, vol. 64, pp. 169–174.

Petralanda et al., *Molecular and Biochemical Parasitology*, 1986, vol. 19, pp. 51–59.

Philipp et al., *The Journal of Immunology*, 1986, vol. 136(7), pp. 2621–2627.

Richer et al., *Experimental Parasitology*, 1992, vol. 75, pp. 213–222.

Robertson et al., *Experimental Parasitology*, 1989, vol. 69, pp. 30–36.

Rogers., *International Journal for Parasitology*, 1982, vol. 12(6), pp. 495–502.

Scott et al., *Acia Tropica*, 1990, vol. 47, pp. 339–353.

Sher et al., *Parasitology*, 1975, vol. 70, pp. 347–357.

Sim et al., Trans. Roy. Soc. Trop. Med. Hyg., 1982, vol. 76(3), pp. 362–370.

Strosburg et al., *Current Opinion in Biotechnology*, 1991, vol. 2, pp. 30–36.

Tamashiro et al., *J Parasitology*., 1987, vol. 73(1), pp. 149–154.

Tanner et al., Trans. Roy. Soc. Trop. Med. Hyg., 1981, vol. 75(1), pp. 173–174.

Wang et al., *Journal of Parenteral Science and Technology*, 1988, vol. 42, pp. S3–S26.

Willadsen et al., *The Journal of Immunology*, 1989, vol. 143(4), pp. 1346–1351.

Wolff et al., Science., 1990, vol. 247, pp. 1465–1468.

Wong et al., *Experimental Parasitology*, 1974, vol. 35, pp. 465–474.

Young et al., Pros. Natl. Acad. Sci. USA, 1983, vol. 80 pp. 1194–1198.

Bini et al., *Electrophoresis*, 1997, vol. 18, pp. 557–562.

Awobuluyi et al., 39$^{th}$ Annual Meeting, *Am J. Trop. Med. Hyg.*, Dec. 1990, Abstract# 150.

Williams, S.A., XP–002152603, Bmaa83513.Emest_Inv3, Acc.No.,A283513, Apr. 5, 1997.

\* cited by examiner

SEQUENCE LISTING

<160> NUMBER OF SEQ ID NOS: 31

<210> SEQ ID NO 1
<211> LENGTH: 29
<212> TYPE: PRT
<213> ORGANISM: Dirofilaria immitis

<400> SEQUENCE: 1

Lys Glu Gly Lys Ala Pro His Phe Pro Gln Gln Gln Val Ala Arg Gln
 1               5                  10                  15

Asn Asp Asp Asp Gly Gly Thr Thr Cys Cys Ile His Arg
                20                  25

<210> SEQ ID NO 2
<211> LENGTH: 16
<212> TYPE: PRT
<213> ORGANISM: Dirofilaria immitis

<400> SEQUENCE: 2

Thr Gly Phe Ser Ala Pro Thr Phe Val Glu Lys Pro Gln Ile Ser Ser
 1               5                  10                  15

<210> SEQ ID NO 3
<211> LENGTH: 332
<212> TYPE: DNA
<213> ORGANISM: Dirofilaria immitis
<220> FEATURE:
<221> NAME/KEY: CDS
<222> LOCATION: (1)..(330)

<400> SEQUENCE: 3 ggt aaa gca cct cat ttc ccg caa cag ccg gta gct cga caa aac gat      48
Gly Lys Ala Pro His Phe Pro Gln Gln Pro Val Ala Arg Gln Asn Asp
 1               5                  10                  15 gat ggg tca ctg gaa ctg gaa tgt ttt tta gaa gct cag cca gtt cca      96
Asp Gly Ser Leu Glu Leu Glu Cys Phe Leu Glu Ala Gln Pro Val Pro
                20                  25                  30 gat att aaa tgg ttt tat gat aca acc gaa cta aaa caa gac cag cgg     144
Asp Ile Lys Trp Phe Tyr Asp Thr Thr Glu Leu Lys Gln Asp Gln Arg
            35                  40                  45 ttc agt ttt cga ctg gat aat aaa gga aac gat gcc tac tca gcc att     192
Phe Ser Phe Arg Leu Asp Asn Lys Gly Asn Asp Ala Tyr Ser Ala Ile
        50                  55                  60 cta caa att aag gat ctt gct gat agt gat gct gga gct tac cga tgt     240
Leu Gln Ile Lys Asp Leu Ala Asp Ser Asp Ala Gly Ala Tyr Arg Cys

```
                65                  70                  75                  80
gct att gta aat cca cac gga aag ggg aat gcc aat ttc aat ctc aaa                288
Ala Ile Val Asn Pro His Gly Lys Gly Asn Ala Asn Phe Asn Leu Lys
                    85                  90                  95 ctc aca ggc ttc tgg gcc cca aca ttt gtc gaa aag cca caa at                     332
Leu Thr Gly Phe Trp Ala Pro Thr Phe Val Glu Lys Pro Gln
                100                 105                 110
```

<210> SEQ ID NO 4
<211> LENGTH: 110
<212> TYPE: PRT
<213> ORGANISM: Dirofilaria immitis

<400> SEQUENCE: 4

```
Gly Lys Ala Pro His Phe Pro Gln Gln Pro Val Ala Arg Gln Asn Asp
 1               5                  10                  15

Asp Gly Ser Leu Glu Leu Glu Cys Phe Leu Glu Ala Gln Pro Val Pro
            20                  25                  30

Asp Ile Lys Trp Phe Tyr Asp Thr Thr Glu Leu Lys Gln Asp Gln Arg
        35                  40                  45

Phe Ser Phe Arg Leu Asp Asn Lys Gly Asn Asp Ala Tyr Ser Ala Ile
    50                  55                  60

Leu Gln Ile Lys Asp Leu Ala Asp Ser Asp Ala Gly Ala Tyr Arg Cys
65                  70                  75                  80

Ala Ile Val Asn Pro His Gly Lys Gly Asn Ala Asn Phe Asn Leu Lys
                85                  90                  95

Leu Thr Gly Phe Trp Ala Pro Thr Phe Val Glu Lys Pro Gln
            100                 105                 110
```

<210> SEQ ID NO 5
<211> LENGTH: 332
<212> TYPE: DNA
<213> ORGANISM: Dirofilaria immitis

<400> SEQUENCE: 5

```
atttgtggct tttcgacaaa tgttggggcc cagaagcctg tgagtttgag attgaaattg         60
gcattcccct ttccgtgtgg atttacaata gcacatcggt aagctccagc atcactatca        120
gcaagatcct taatttgtag aatggctgag taggcatcgt ttcctttatt atccagtcga        180
aaactgaacc gctggtcttg ttttagttcg gttgtatcat aaaaccattt aatatctgga        240
actggctgag cttctaaaaa acattccagt tccagtgacc catcatcgtt ttgtcgagct        300
accggctgtt gcgggaaatg aggtgcttta cc                                       332
```

<210> SEQ ID NO 6
<211> LENGTH: 775
<212> TYPE: DNA
<213> ORGANISM: Dirofilaria immitis
<220> FEATURE:
<221> NAME/KEY: CDS
<222> LOCATION: (1)..(696)

<400> SEQUENCE: 6

```
gga aag ggg aat gcc aat ttc aat ctc aaa ctc aca ggc ttc tgg gcc            48
Gly Lys Gly Asn Ala Asn Phe Asn Leu Lys Leu Thr Gly Phe Trp Ala
 1               5                  10                  15 cca aca ttt gtc gaa aag cca caa ata tca tct cgt gat gat ggt caa            96
Pro Thr Phe Val Glu Lys Pro Gln Ile Ser Ser Arg Asp Asp Gly Gln
            20                  25                  30 gtt atg gtt atg gaa ttc aga gca aag tca att ctc atg cct act ttt          144
Val Met Val Met Glu Phe Arg Ala Lys Ser Ile Leu Met Pro Thr Phe
```

-continued

```
                Val Met Val Met Glu Phe Arg Ala Lys Ser Ile Leu Met Pro Thr Phe
                             35                  40                  45 gtc tgg caa aag ggt gaa gaa atc gta gct gaa tcg gat cga gtg aga                 192
Val Trp Gln Lys Gly Glu Glu Ile Val Ala Glu Ser Asp Arg Val Arg
 50                  55                  60 att gtt cta ata gaa gag gca aat caa acg tat tat gct gct ctg gaa                 240
Ile Val Leu Ile Glu Glu Ala Asn Gln Thr Tyr Tyr Ala Ala Leu Glu
 65                  70                  75                  80 att aag gag ccg acg aaa gaa aaa gat gcg ggc caa ttt gtt tgc aca                 288
Ile Lys Glu Pro Thr Lys Glu Lys Asp Ala Gly Gln Phe Val Cys Thr
                 85                  90                  95 gcg aaa aat gaa tct gga aaa tta aca gcc act ttt act gtt aaa ttt                 336
Ala Lys Asn Glu Ser Gly Lys Leu Thr Ala Thr Phe Thr Val Lys Phe
                100                 105                 110 gaa gtt cca caa gga gct cca acc ttt act cgt aaa cca cag att ttg                 384
Glu Val Pro Gln Gly Ala Pro Thr Phe Thr Arg Lys Pro Gln Ile Leu
            115                 120                 125 caa aaa aca tca gat tct ggt gat cca gcc att gtc ttt gat att gga                 432
Gln Lys Thr Ser Asp Ser Gly Asp Pro Ala Ile Val Phe Asp Ile Gly
        130                 135                 140 ttc caa gct gat cag aac cca ggg gtt att tgg ttg aat cca aaa ggc                 480
Phe Gln Ala Asp Gln Asn Pro Gly Val Ile Trp Leu Asn Pro Lys Gly
145                 150                 155                 160 aaa aaa atg aag gaa tca agt cgt ata aag ttt gga tta aca cct gat                 528
Lys Lys Met Lys Glu Ser Ser Arg Ile Lys Phe Gly Leu Thr Pro Asp
                165                 170                 175 ggt ggt gca aat acg ttc act gct cag cta gaa ctg aaa aat tat aaa                 576
Gly Gly Ala Asn Thr Phe Thr Ala Gln Leu Glu Leu Lys Asn Tyr Lys
            180                 185                 190 gca aaa gac agt ggt aca tat acc tgc aat atc aag aat gaa gct ggt                 624
Ala Lys Asp Ser Gly Thr Tyr Thr Cys Asn Ile Lys Asn Glu Ala Gly
        195                 200                 205 gaa gca aac gtc gaa ttg aca ttg aat atc gaa gga ccc tta gac gaa                 672
Glu Ala Asn Val Glu Leu Thr Leu Asn Ile Glu Gly Pro Leu Asp Glu
    210                 215                 220 gga gca gat gat gct agc gaa gcg tgaaatggac aagttttagg cggtccacaa               726
Gly Ala Asp Asp Ala Ser Glu Ala
225                 230 tttgctggat cctatgaaaa aaaaaaaaaa aaaaaaaaaa aaaaaaaa                             775
```

<210> SEQ ID NO 7
<211> LENGTH: 232
<212> TYPE: PRT
<213> ORGANISM: Dirofilaria immitis

<400> SEQUENCE: 7

```
Gly Lys Gly Asn Ala Asn Phe Asn Leu Lys Leu Thr Gly Phe Trp Ala
 1               5                  10                  15

Pro Thr Phe Val Glu Lys Pro Gln Ile Ser Ser Arg Asp Asp Gly Gln
                20                  25                  30

Val Met Val Met Glu Phe Arg Ala Lys Ser Ile Leu Met Pro Thr Phe
             35                  40                  45

Val Trp Gln Lys Gly Glu Glu Ile Val Ala Glu Ser Asp Arg Val Arg
 50                  55                  60

Ile Val Leu Ile Glu Glu Ala Asn Gln Thr Tyr Tyr Ala Ala Leu Glu
 65                  70                  75                  80

Ile Lys Glu Pro Thr Lys Glu Lys Asp Ala Gly Gln Phe Val Cys Thr
                 85                  90                  95
```

```
Ala Lys Asn Glu Ser Gly Lys Leu Thr Ala Thr Phe Thr Val Lys Phe
            100                 105                 110

Glu Val Pro Gln Gly Ala Pro Thr Phe Thr Arg Lys Pro Gln Ile Leu
        115                 120                 125

Gln Lys Thr Ser Asp Ser Gly Asp Pro Ala Ile Val Phe Asp Ile Gly
    130                 135                 140

Phe Gln Ala Asp Gln Asn Pro Gly Val Ile Trp Leu Asn Pro Lys Gly
145                 150                 155                 160

Lys Lys Met Lys Glu Ser Ser Arg Ile Lys Phe Gly Leu Thr Pro Asp
                165                 170                 175

Gly Gly Ala Asn Thr Phe Thr Ala Gln Leu Glu Leu Lys Asn Tyr Lys
            180                 185                 190

Ala Lys Asp Ser Gly Thr Tyr Thr Cys Asn Ile Lys Asn Glu Ala Gly
        195                 200                 205

Glu Ala Asn Val Glu Leu Thr Leu Asn Ile Glu Gly Pro Leu Asp Glu
    210                 215                 220

Gly Ala Asp Asp Ala Ser Glu Ala
225                 230

<210> SEQ ID NO 8
<211> LENGTH: 775
<212> TYPE: DNA
<213> ORGANISM: Dirofilaria immitis

<400> SEQUENCE: 8
tttttttttt tttttttttt tttttttttt tttcatagga tccagcaaat tgtggaccgc      60
ctaaaacttg tccatttcac gcttcgctag catcatctgc tccttcgtct aagggtcctt    120
cgatattcaa tgtcaattcg acgtttgctt caccagcttc attcttgata ttgcaggtat    180
atgtaccact gtcttttgct ttataatttt tcagttctag ctgagcagtg aacgtatttg    240
caccaccatc aggtgttaat ccaaacttta tacgacttga ttccttcatt tttttgcctt    300
ttggattcaa ccaaataacc cctgggttct gatcagcttg gaatccaata tcaaagacaa    360
tggctggatc accagaatct gatgtttttt gcaaaatctg tggtttacga gtaaaggttg    420
gagctccttg tggaacttca aatttaacag taaaagtggc tgttaatttt ccagattcat    480
ttttcgctgt gcaaacaaat ggcccgcat cttttttcttt cgtcggctcc ttaatttcca    540
gagcagcata atacgtttga tttgcctctt ctattagaac aattctcact cgatccgatt    600
cagctacgat ttcttcaccc ttttgccaga caaaagtagg catgagaatt gactttgctc    660
tgaattccat aaccataact tgaccatcat cacgagatga tatttgtggc ttttcgacaa    720
atgttggggc ccagaagcct gtgagtttga gattgaaatt ggcattcccc tttcc         775

<210> SEQ ID NO 9
<211> LENGTH: 699
<212> TYPE: DNA
<213> ORGANISM: Dirofilaria immitis

<400> SEQUENCE: 9
ggaaagggga atgccaattt caatctcaaa ctcacaggct tctgggcccc aacatttgtc      60
gaaaagccac aaatatcatc tcgtgatgat ggtcaagtta tggttatgga attcagagca    120
aagtcaattc tcatgcctac ttttgtctgg caaaagggtg aagaaatcgt agctgaatcg    180
gatcgagtga gaattgttct aatagaagag gcaaatcaaa cgtattatgc tgctctggaa    240
attaaggagc cgacgaaaga aaaagatgcg ggccaatttg tttgcacagc gaaaaatgaa    300
```

-continued

```
tctggaaaat taacagccac ttttactgtt aaatttgaag ttccacaagg agctccaacc    360
tttactcgta aaccacagat tttgcaaaaa acatcagatt ctggtgatcc agccattgtc    420
tttgatattg gattccaagc tgatcagaac ccaggggtta tttggttgaa tccaaaaggc    480
aaaaaaatga aggaatcaag tcgtataaag tttggattaa cacctgatgg tggtgcaaat    540
acgttcactg ctcagctaga actgaaaaat tataaagcaa aagacagtgg tacatatacc    600
tgcaatatca agaatgaagc tggtgaagca aacgtcgaat tgacattgaa tatcgaagga    660
cccttagacg aaggagcaga tgatgctagc gaagcgtga                           699
```

<210> SEQ ID NO 10
<211> LENGTH: 699
<212> TYPE: DNA
<213> ORGANISM: Dirofilaria immitis

<400> SEQUENCE: 10

```
tcacgcttcg ctagcatcat ctgctccttc gtctaagggt ccttcgatat tcaatgtcaa     60
ttcgacgttt gcttcaccag cttcattctt gatattgcag gtatatgtac cactgtcttt    120
tgctttataa ttttttcagtt ctagctgagc agtgaacgta tttgcaccac catcaggtgt   180
taatccaaac tttatacgac ttgattcctt cattttttg ccttttggat tcaaccaaat    240 aaccccctggg ttctgatcag cttggaatcc aatatcaaaa acaatggctg gatcaccaga   300
atctgatgtt ttttgcaaaa tctgtggttt acgagtaaag gttggagctc cttgtggaac    360
ttcaaattta acagtaaaag tggctgttaa ttttccagat tcattttctcg ctgtgcaaac  420 aaattggccc gcatctttt ctttcgtcgg ctccttaatt tccagagcag cataatacgt    480
ttgatttgcc tcttctatta gaacaattct cactcgatcc gattcagcta cgatttcttc    540
acccttttgc cagacaaaag taggcatgag aattgacttt gctctgaatt ccataaccat    600
aacttgacca tcatcacgag atgatatttg tggcttttcg acaaatgttg gggcccagaa    660
gcctgtgagt ttgagattga aattggcatt ccccttttcc                          699
```

<210> SEQ ID NO 11
<211> LENGTH: 376
<212> TYPE: DNA
<213> ORGANISM: Dirofilaria immitis
<220> FEATURE:
<221> NAME/KEY: CDS
<222> LOCATION: (65)..(376)

<400> SEQUENCE: 11

```
ggtttaatta cccaagtttg aggattcctg cgggcggcaa ctaataaagc tagctattaa     60 aaag atg ccg gag ggt aaa gca cct cat ttc ccg caa cag ccg gta gct    109
     Met Pro Glu Gly Lys Ala Pro His Phe Pro Gln Gln Pro Val Ala
       1               5                  10                  15 cga caa aac gat gat ggg tca ctg gaa ctg gaa tgt ttt tta gaa gct    157
Arg Gln Asn Asp Asp Gly Ser Leu Glu Leu Glu Cys Phe Leu Glu Ala
                20                  25                  30 cag cca gtt cca gat att aaa tgg ttt tat gat aca acc gaa cta aaa    205
Gln Pro Val Pro Asp Ile Lys Trp Phe Tyr Asp Thr Thr Glu Leu Lys
            35                  40                  45 caa gac cag cgg ttc agt ttt cga ctg gat aat aaa gga aac gat gcc    253
Gln Asp Gln Arg Phe Ser Phe Arg Leu Asp Asn Lys Gly Asn Asp Ala
        50                  55                  60 tac tca gcc att cta caa att aag gat ctt gct gat agt gat gct gga    301
Tyr Ser Ala Ile Leu Gln Ile Lys Asp Leu Ala Asp Ser Asp Ala Gly
    65                  70                  75
```

```
gct tac cga tgt gct att gta aat cca cac gga aag ggg aat gcc aat    349
Ala Tyr Arg Cys Ala Ile Val Asn Pro His Gly Lys Gly Asn Ala Asn
 80              85                  90                  95 ttc aat ctc aaa ctc aca ggc ttc tgg                                376
Phe Asn Leu Lys Leu Thr Gly Phe Trp
            100
```

<210> SEQ ID NO 12
<211> LENGTH: 104
<212> TYPE: PRT
<213> ORGANISM: Dirofilaria immitis

<400> SEQUENCE: 12

```
Met Pro Glu Gly Lys Ala Pro His Phe Pro Gln Gln Pro Val Ala Arg
  1               5                  10                  15

Gln Asn Asp Asp Gly Ser Leu Glu Leu Glu Cys Phe Leu Glu Ala Gln
                 20                  25                  30

Pro Val Pro Asp Ile Lys Trp Phe Tyr Asp Thr Thr Glu Leu Lys Gln
             35                  40                  45

Asp Gln Arg Phe Ser Phe Arg Leu Asp Asn Lys Gly Asn Asp Ala Tyr
         50                  55                  60

Ser Ala Ile Leu Gln Ile Lys Asp Leu Ala Asp Ser Asp Ala Gly Ala
 65                  70                  75                  80

Tyr Arg Cys Ala Ile Val Asn Pro His Gly Lys Gly Asn Ala Asn Phe
                 85                  90                  95

Asn Leu Lys Leu Thr Gly Phe Trp
            100
```

<210> SEQ ID NO 13
<211> LENGTH: 376
<212> TYPE: DNA
<213> ORGANISM: Dirofilaria immitis

<400> SEQUENCE: 13

```
ccagaagcct gtgagtttga gattgaaatt ggcattcccc tttccgtgtg gatttacaat      60
agcacatcgg taagctccag catcactatc agcaagatcc ttaatttgta gaatggctga     120
gtaggcatcg tttcctttat tatccagtcg aaaactgaac cgctggtctt gttttagttc     180
ggttgtatca taaaaccatt taatatctgg aactggctga gcttctaaaa aacattccag     240
ttccagtgac ccatcatcgt tttgtcgagc taccggctgt gcgggaaat gaggtgcttt      300
accctccggc atcttttaa tagctagctt tattagttgc cgcccgcagg aatcctcaaa     360
cttgggtaat taaacc                                                    376
```

<210> SEQ ID NO 14
<211> LENGTH: 312
<212> TYPE: DNA
<213> ORGANISM: Dirofilaria immitis

<400> SEQUENCE: 14

```
atgccggagg gtaaagcacc tcatttcccg caacagccgg tagctcgaca aaacgatgat      60
gggtcactgg aactggaatg ttttttagaa gctcagccag ttccagatat taaatggttt     120
tatgatacaa ccgaactaaa acaagaccag cggttcagtt ttcgactgga taataaagga     180
aacgatgcct actcagccat tctacaaatt aaggatcttg ctgatagtga tgctggagct     240
taccgatgtg ctattgtaaa tccacacgga aaggggaatg ccaatttcaa tctcaaactc     300
acaggcttct gg                                                        312
```

<210> SEQ ID NO 15
<211> LENGTH: 312
<212> TYPE: DNA
<213> ORGANISM: Dirofilaria immitis

<400> SEQUENCE: 15

| | | |
|---|---|---|
| ccagaagcct gtgagtttga gattgaaatt ggcattcccc tttccgtgtg gatttacaat | 60 |
| agcacatcgg taagctccag catcactatc agcaagatcc ttaatttgta gaatggctga | 120 |
| gtaggcatcg tttcctttat tatccagtcg aaaactgaac cgctggtctt gttttagttc | 180 |
| ggttgtatca taaaaccatt taatatctgg aactggctga gcttctaaaa aacattccag | 240 |
| ttccagtgac ccatcatcgt tttgtcgagc taccggctgt tgcgggaaat gaggtgcttt | 300 |
| accctccggc at | 312 |

<210> SEQ ID NO 16
<211> LENGTH: 1106
<212> TYPE: DNA
<213> ORGANISM: Dirofilaria immitis
<220> FEATURE:
<221> NAME/KEY: CDS
<222> LOCATION: (65)..(1027)

<400> SEQUENCE: 16

```
ggtttaatta cccaagtttg aggattcctg cgggcggcaa ctaataaagc tagctattaa          60 aaag atg ccg gag ggt aaa gca cct cat ttc ccg caa cag ccg gta gct         109
     Met Pro Glu Gly Lys Ala Pro His Phe Pro Gln Gln Pro Val Ala
      1               5                  10                  15 cga caa aac gat gat ggg tca ctg gaa ctg gaa tgt ttt tta gaa gct         157
Arg Gln Asn Asp Asp Gly Ser Leu Glu Leu Glu Cys Phe Leu Glu Ala
             20                  25                  30 cag cca gtt cca gat att aaa tgg ttt tat gat aca acc gaa cta aaa         205
Gln Pro Val Pro Asp Ile Lys Trp Phe Tyr Asp Thr Thr Glu Leu Lys
         35                  40                  45 caa gac cag cgg ttc agt ttt cga ctg gat aat aaa gga aac gat gcc         253
Gln Asp Gln Arg Phe Ser Phe Arg Leu Asp Asn Lys Gly Asn Asp Ala
     50                  55                  60 tac tca gcc att cta caa att aag gat ctt gct gat agt gat gct gga         301
Tyr Ser Ala Ile Leu Gln Ile Lys Asp Leu Ala Asp Ser Asp Ala Gly
 65                  70                  75 gct tac cga tgt gct att gta aat cca cac gga aag ggg aat gcc aat         349
Ala Tyr Arg Cys Ala Ile Val Asn Pro His Gly Lys Gly Asn Ala Asn
             80                  85                  90                  95 ttc aat ctc aaa ctc aca ggc ttc tgg gcc cca aca ttt gtc gaa aag         397
Phe Asn Leu Lys Leu Thr Gly Phe Trp Ala Pro Thr Phe Val Glu Lys
                100                 105                 110 cca caa ata tca tct cgt gat gat ggt caa gtt atg gtt atg gaa ttc         445
Pro Gln Ile Ser Ser Arg Asp Asp Gly Gln Val Met Val Met Glu Phe
            115                 120                 125 aga gca aag tca att ctc atg cct act ttt gtc tgg caa aag ggt gaa         493
Arg Ala Lys Ser Ile Leu Met Pro Thr Phe Val Trp Gln Lys Gly Glu
        130                 135                 140 gaa atc gta gct gaa tcg gat cga gtg aga att gtt cta ata gaa gag         541
Glu Ile Val Ala Glu Ser Asp Arg Val Arg Ile Val Leu Ile Glu Glu
    145                 150                 155 gca aat caa acg tat tat gct gct ctg gaa att aag gag ccg acg aaa         589
Ala Asn Gln Thr Tyr Tyr Ala Ala Leu Glu Ile Lys Glu Pro Thr Lys
160                 165                 170                 175 gaa aaa gat gcg ggc caa ttt gtt tgc aca gcg aaa aat gaa tct gga         637
Glu Lys Asp Ala Gly Gln Phe Val Cys Thr Ala Lys Asn Glu Ser Gly
```

-continued

```
aaa tta aca gcc act ttt act gtt aaa ttt gaa gtt cca caa gga gct        685
Lys Leu Thr Ala Thr Phe Thr Val Lys Phe Glu Val Pro Gln Gly Ala
            195                 200                 205 cca acc ttt act cgt aaa cca cag att ttg caa aaa aca tca gat tct        733
Pro Thr Phe Thr Arg Lys Pro Gln Ile Leu Gln Lys Thr Ser Asp Ser
        210                 215                 220 ggt gat cca gcc att gtc ttt gat att gga ttc caa gct gat cag aac        781
Gly Asp Pro Ala Ile Val Phe Asp Ile Gly Phe Gln Ala Asp Gln Asn
    225                 230                 235 cca ggg gtt att tgg ttg aat cca aaa ggc aaa aaa atg aag gaa tca        829
Pro Gly Val Ile Trp Leu Asn Pro Lys Gly Lys Lys Met Lys Glu Ser
240                 245                 250                 255 agt cgt ata aag ttt gga tta aca cct gat ggt ggt gca aat acg ttc        877
Ser Arg Ile Lys Phe Gly Leu Thr Pro Asp Gly Gly Ala Asn Thr Phe
                260                 265                 270 act gct cag cta gaa ctg aaa aat tat aaa gca aaa gac agt ggt aca        925
Thr Ala Gln Leu Glu Leu Lys Asn Tyr Lys Ala Lys Asp Ser Gly Thr
            275                 280                 285 tat acc tgc aat atc aag aat gaa gct ggt gaa gca aac gtc gaa ttg        973
Tyr Thr Cys Asn Ile Lys Asn Glu Ala Gly Glu Ala Asn Val Glu Leu
        290                 295                 300 aca ttg aat atc gaa gga ccc tta gac gaa gga gca gat gat gct agc       1021
Thr Leu Asn Ile Glu Gly Pro Leu Asp Glu Gly Ala Asp Asp Ala Ser
    305                 310                 315 gaa gcg tgaaatggac aagttttagg cggtccacaa tttgctggat cctatgaaaa       1077
Glu Ala
320 aaaaaaaaaa aaaaaaaaa aaaaaaaaa                                         1106
```

<210> SEQ ID NO 17
<211> LENGTH: 321
<212> TYPE: PRT
<213> ORGANISM: Dirofilaria immitis

<400> SEQUENCE: 17

```
Met Pro Glu Gly Lys Ala Pro His Phe Pro Gln Gln Pro Val Ala Arg
 1               5                  10                  15

Gln Asn Asp Asp Gly Ser Leu Glu Leu Glu Cys Phe Leu Glu Ala Gln
            20                  25                  30

Pro Val Pro Asp Ile Lys Trp Phe Tyr Asp Thr Thr Glu Leu Lys Gln
        35                  40                  45

Asp Gln Arg Phe Ser Phe Arg Leu Asp Asn Lys Gly Asn Asp Ala Tyr
    50                  55                  60

Ser Ala Ile Leu Gln Ile Lys Asp Leu Ala Asp Ser Asp Ala Gly Ala
65                  70                  75                  80

Tyr Arg Cys Ala Ile Val Asn Pro His Gly Lys Gly Asn Ala Asn Phe
                85                  90                  95

Asn Leu Lys Leu Thr Gly Phe Trp Ala Pro Thr Phe Val Glu Lys Pro
            100                 105                 110

Gln Ile Ser Ser Arg Asp Asp Gly Gln Val Met Val Met Glu Phe Arg
        115                 120                 125

Ala Lys Ser Ile Leu Met Pro Thr Phe Val Trp Gln Lys Gly Glu Glu
    130                 135                 140

Ile Val Ala Glu Ser Asp Arg Val Arg Ile Val Leu Ile Glu Glu Ala
145                 150                 155                 160

Asn Gln Thr Tyr Tyr Ala Ala Leu Glu Ile Lys Glu Pro Thr Lys Glu
```

```
                    165                 170                 175
Lys Asp Ala Gly Gln Phe Val Cys Thr Ala Lys Asn Glu Ser Gly Lys
                180                 185                 190

Leu Thr Ala Thr Phe Thr Val Lys Phe Glu Val Pro Gln Gly Ala Pro
            195                 200                 205

Thr Phe Thr Arg Lys Pro Gln Ile Leu Gln Lys Thr Ser Asp Ser Gly
        210                 215                 220

Asp Pro Ala Ile Val Phe Asp Ile Gly Phe Gln Ala Asp Gln Asn Pro
225                 230                 235                 240

Gly Val Ile Trp Leu Asn Pro Lys Gly Lys Met Lys Glu Ser Ser
                245                 250                 255

Arg Ile Lys Phe Gly Leu Thr Pro Asp Gly Gly Ala Asn Thr Phe Thr
                260                 265                 270

Ala Gln Leu Glu Leu Lys Asn Tyr Lys Ala Lys Asp Ser Gly Thr Tyr
            275                 280                 285

Thr Cys Asn Ile Lys Asn Glu Ala Gly Glu Ala Asn Val Glu Leu Thr
        290                 295                 300

Leu Asn Ile Glu Gly Pro Leu Asp Glu Gly Ala Asp Asp Ala Ser Glu
305                 310                 315                 320

Ala
```

<210> SEQ ID NO 18
<211> LENGTH: 1106
<212> TYPE: DNA
<213> ORGANISM: Dirofilaria immitis

<400> SEQUENCE: 18

```
tttttttttt tttttttttt tttttttttt tttcatagga tccagcaaat tgtggaccgc      60
ctaaaacttg tccatttcac gcttcgctag catcatctgc tccttcgtct aagggtcctt     120
cgatattcaa tgtcaattcg acgtttgctt caccagcttc attcttgata ttgcaggtat     180
atgtaccact gtcttttgct ttataatttt tcagttctag ctgagcagtg aacgtatttg     240
caccaccatc aggtgttaat ccaaacttta tacgacttga ttccttcatt ttttttgcctt     300
ttggattcaa ccaaataacc cctgggttct gatcagcttg gaatccaata tcaaagacaa     360
tggctggatc accagaatct gatgttttt gcaaaatctg tggtttacga gtaaaggttg     420
gagctccttg tggaacttca aatttaacag taaaagtggc tgttaatttt ccagattcat     480
ttttcgctgt gcaaacaaat tggcccgcat cttttttctt cgtcggctcc ttaatttcca     540
gagcagcata atacgtttga tttgcctctt ctattagaac aattctcact cgatccgatt     600
cagctacgat ttcttcaccc ttttgccaga caaagtagg catgagaatt gactttgctc     660
tgaattccat aaccataact tgaccatcat cacgagatga tatttgtggc ttttcgacaa     720
atgttggggc ccagaagcct gtgagtttga gattgaaatt ggcattcccc tttccgtgtg     780
gatttacaat agcacatcgg taagctccag catcactatc agcaagatcc ttaatttgta     840
gaatggctga gtaggcatcg tttcctttat tatccagtcg aaaactgaac cgctggtctt     900
gttttagttc ggttgtatca taaaaccatt taatatctgg aactggctga gcttctaaaa     960
aacattccag ttccagtgac ccatcatcgt tttgtcgagc taccggctgt tgcgggaaat    1020
gaggtgcttt accctccggc atcttttaa tagctagctt tattagttgc cgcccgcagg    1080
aatcctcaaa cttgggtaat taaacc                                         1106
```

<210> SEQ ID NO 19

<211> LENGTH: 966
<212> TYPE: DNA
<213> ORGANISM: Dirofilaria immitis

<400> SEQUENCE: 19

| | | | | | |
|---|---|---|---|---|---|
| atgccggagg | gtaaagcacc | tcatttcccg | caacagccgg | tagctcgaca | aaacgatgat | 60 |
| gggtcactgg | aactggaatg | ttttttagaa | gctcagccag | ttccagatat | taaatggttt | 120 |
| tatgatacaa | ccgaactaaa | acaagaccag | cggttcagtt | ttcgactgga | taataaagga | 180 |
| aacgatgcct | actcagccat | tctacaaatt | aaggatcttg | ctgatagtga | tgctggagct | 240 |
| taccgatgtg | ctattgtaaa | tccacacgga | aaggggaatg | ccaatttcaa | tctcaaactc | 300 |
| acaggcttct | gggccccaac | atttgtcgaa | agccacaaa | tatcatctcg | tgatgatggt | 360 |
| caagttatgg | ttatggaatt | cagagcaaag | tcaattctca | tgcctacttt | tgtctggcaa | 420 |
| aagggtgaag | aaatcgtagc | tgaatcggat | cgagtgagaa | ttgttctaat | agaagaggca | 480 |
| aatcaaacgt | attatgctgc | tctggaaatt | aaggagccga | cgaaagaaaa | agatgcgggc | 540 |
| caatttgttt | gcacagcgaa | aaatgaatct | ggaaaattaa | cagccacttt | tactgttaaa | 600 |
| tttgaagttc | cacaaggagc | tccaaccttt | actcgtaaac | cacagatttt | gcaaaaaaca | 660 |
| tcagattctg | gtgatccagc | cattgtcttt | gatattggat | tccaagctga | tcagaaccca | 720 |
| ggggttattt | ggttgaatcc | aaaaggcaaa | aaaatgaagg | aatcaagtcg | tataaagttt | 780 |
| ggattaacac | ctgatggtgg | tgcaaatacg | ttcactgctc | agctagaact | gaaaaattat | 840 |
| aaagcaaaag | acagtggtac | atatacctgc | aatatcaaga | atgaagctgg | tgaagcaaac | 900 |
| gtcgaattga | cattgaatat | cgaaggaccc | ttagacgaag | gagcagatga | tgctagcgaa | 960 |
| gcgtga | | | | | 966 |

<210> SEQ ID NO 20
<211> LENGTH: 966
<212> TYPE: DNA
<213> ORGANISM: Dirofilaria immitis

<400> SEQUENCE: 20

| | | | | | |
|---|---|---|---|---|---|
| tcacgcttcg | ctagcatcat | ctgctccttc | gtctaagggt | ccttcgatat | tcaatgtcaa | 60 |
| ttcgacgttt | gcttcaccag | cttcattctt | gatattgcag | gtatatgtac | cactgtcttt | 120 |
| tgctttataa | ttttttcagtt | ctagctgagc | agtgaacgta | tttgcaccac | catcaggtgt | 180 |
| taatccaaac | tttatacgac | ttgattcctt | cattttttg | cctttggat | tcaaccaaat | 240 |
| aaccctgggt | tctgatcagc | ttggaatcc | aatatcaaag | acaatggctg | gatcaccaga | 300 |
| atctgatgtt | ttttgcaaaa | tctgtggttt | acgagtaaag | gttggagctc | cttgtggaac | 360 |
| ttcaaattta | acagtaaaag | tggctgttaa | ttttccagat | tcattttttcg | ctgtgcaaac | 420 |
| aaattggccc | gcatcttttt | ctttcgtcgg | ctccttaatt | tccagagcag | cataatacgt | 480 |
| ttgatttgcc | tcttctatta | gaacaattct | cactcgatcc | gattcagcta | cgatttcttc | 540 |
| acccttttgc | cagacaaaag | taggcatgag | aattgacttt | gctctgaatt | ccataaccat | 600 |
| aacttgacca | tcatcacgag | atgatatttg | tggcttttcg | acaaatgttg | ggcccagaa | 660 |
| gcctgtgagt | ttgagattga | aattggcatt | cccctttccg | tgtggattta | caatagcaca | 720 |
| tcggtaagct | ccagcatcac | tatcagcaag | atccttaatt | tgtagaatgg | ctgagtaggc | 780 |
| atcgttccct | ttattatcca | gtcgaaaact | gaaccgctgg | tcttgtttta | gttcggttgt | 840 |
| atcataaaac | catttaatat | ctggaactgg | ctgagcttct | aaaaaacatt | ccagttccag | 900 |
| tgacccatca | tcgttttgtc | gagctaccgg | ctgttgcggg | aaatgaggtg | ctttacccct | 960 |

```
cggcat                                                              966

<210> SEQ ID NO 21
<211> LENGTH: 989
<212> TYPE: DNA
<213> ORGANISM: Dirofilaria immitis
<220> FEATURE:
<221> NAME/KEY: CDS
<222> LOCATION: (13)..(975)

<400> SEQUENCE: 21
ccgagctcga ga atg ccg gag ggt aaa gca cct cat ttc ccg caa cag ccg    51
           Met Pro Glu Gly Lys Ala Pro His Phe Pro Gln Gln Pro
             1               5                  10 gta gct cga caa aac gat gat ggg tca ctg gaa ctg gaa tgt ttt tta     99
Val Ala Arg Gln Asn Asp Asp Gly Ser Leu Glu Leu Glu Cys Phe Leu
     15                  20                  25 gaa gct cag cca gtt cca gat att aaa tgg ttt tat gat aca acc gaa    147
Glu Ala Gln Pro Val Pro Asp Ile Lys Trp Phe Tyr Asp Thr Thr Glu
 30                  35                  40                  45 cta aaa caa gac cag cgg ttc agt ttt cga ctg gat aat aaa gga aac    195
Leu Lys Gln Asp Gln Arg Phe Ser Phe Arg Leu Asp Asn Lys Gly Asn
             50                  55                  60 gat gcc tac tca gcc att cta caa att aag gat ctt gct gat agt gat    243
Asp Ala Tyr Ser Ala Ile Leu Gln Ile Lys Asp Leu Ala Asp Ser Asp
         65                  70                  75 gct gga gct tac cga tgt gct att gta aat cca cac gga aag ggg aat    291
Ala Gly Ala Tyr Arg Cys Ala Ile Val Asn Pro His Gly Lys Gly Asn
     80                  85                  90 gcc aat ttc aat ctc aaa ctc aca ggc ttc tgg gcc cca aca ttt gtc    339
Ala Asn Phe Asn Leu Lys Leu Thr Gly Phe Trp Ala Pro Thr Phe Val
 95                 100                 105 gaa aag cca caa ata tca tct cgt gat gat ggt caa gtt atg gtt atg    387
Glu Lys Pro Gln Ile Ser Ser Arg Asp Asp Gly Gln Val Met Val Met
110                 115                 120                 125 gaa ttc aga gca aag tca att ctc atg cct act ttt gtc tgg caa aag    435
Glu Phe Arg Ala Lys Ser Ile Leu Met Pro Thr Phe Val Trp Gln Lys
             130                 135                 140 ggt gaa gaa atc gta gct gaa tcg gat cga gtg aga att gtt cta ata    483
Gly Glu Glu Ile Val Ala Glu Ser Asp Arg Val Arg Ile Val Leu Ile
         145                 150                 155 gaa gag gca aat caa acg tat tat gct gct ctg gaa att aag gag ccg    531
Glu Glu Ala Asn Gln Thr Tyr Tyr Ala Ala Leu Glu Ile Lys Glu Pro
     160                 165                 170 acg aaa gaa aaa gat gcg ggc caa ttt gtt tgc aca gcg aaa aat gaa    579
Thr Lys Glu Lys Asp Ala Gly Gln Phe Val Cys Thr Ala Lys Asn Glu
175                 180                 185 tct gga aaa tta aca gcc act ttt act gtt aaa ttt gaa gtt cca caa    627
Ser Gly Lys Leu Thr Ala Thr Phe Thr Val Lys Phe Glu Val Pro Gln
190                 195                 200                 205 gga gct cca acc ttt act cgt aaa cca cag att ttg caa aaa aca tca    675
Gly Ala Pro Thr Phe Thr Arg Lys Pro Gln Ile Leu Gln Lys Thr Ser
             210                 215                 220 gat tct ggt gat cca gcc att gtc ttt gat att gga ttc caa gct gat    723
Asp Ser Gly Asp Pro Ala Ile Val Phe Asp Ile Gly Phe Gln Ala Asp
         225                 230                 235 cag aac cca ggg gtt att tgg ttg aat cca aaa ggc aaa aaa atg aag    771
Gln Asn Pro Gly Val Ile Trp Leu Asn Pro Lys Gly Lys Lys Met Lys
     240                 245                 250 gaa tca agt cgt ata aag ttt gga tta aca cct gat ggt ggt gca aat    819
```

| | | | | | | | | | | | | |
|---|---|---|---|---|---|---|---|---|---|---|---|---|
|Glu|Ser|Ser|Arg|Ile|Lys|Phe|Gly|Leu|Thr|Pro|Asp|Gly|Gly|Ala|Asn|
| |255| | | |260| | | |265| | | | | | |

```
acg ttc act gct cag cta gaa ctg aaa aat tat aaa gca aaa gac agt     867
Thr Phe Thr Ala Gln Leu Glu Leu Lys Asn Tyr Lys Ala Lys Asp Ser
270                 275                 280                 285 ggt aca tat acc tgc aat atc aag aat gaa gct ggt gaa gca aac gtc     915
Gly Thr Tyr Thr Cys Asn Ile Lys Asn Glu Ala Gly Glu Ala Asn Val
                290                 295                 300 gaa ttg aca ttg aat atc gaa gga ccc tta gac gaa gga gca gat gat     963
Glu Leu Thr Leu Asn Ile Glu Gly Pro Leu Asp Glu Gly Ala Asp Asp
            305                 310                 315 gct agc gaa gcg tgatctgcag ctgg                                     989
Ala Ser Glu Ala
        320
```

<210> SEQ ID NO 22
<211> LENGTH: 321
<212> TYPE: PRT
<213> ORGANISM: Dirofilaria immitis

<400> SEQUENCE: 22

```
Met Pro Glu Gly Lys Ala Pro His Phe Pro Gln Gln Pro Val Ala Arg
 1               5                  10                  15

Gln Asn Asp Asp Gly Ser Leu Glu Leu Glu Cys Phe Leu Glu Ala Gln
                20                  25                  30

Pro Val Pro Asp Ile Lys Trp Phe Tyr Asp Thr Thr Glu Leu Lys Gln
            35                  40                  45

Asp Gln Arg Phe Ser Phe Arg Leu Asp Asn Lys Gly Asn Asp Ala Tyr
        50                  55                  60

Ser Ala Ile Leu Gln Ile Lys Asp Leu Ala Asp Ser Asp Ala Gly Ala
65                  70                  75                  80

Tyr Arg Cys Ala Ile Val Asn Pro His Gly Lys Gly Asn Ala Asn Phe
                85                  90                  95

Asn Leu Lys Leu Thr Gly Phe Trp Ala Pro Thr Phe Val Glu Lys Pro
            100                 105                 110

Gln Ile Ser Ser Arg Asp Asp Gly Gln Val Met Val Met Glu Phe Arg
        115                 120                 125

Ala Lys Ser Ile Leu Met Pro Thr Phe Val Trp Gln Lys Gly Glu Glu
    130                 135                 140

Ile Val Ala Glu Ser Asp Arg Val Arg Ile Val Leu Ile Glu Glu Ala
145                 150                 155                 160

Asn Gln Thr Tyr Tyr Ala Ala Leu Glu Ile Lys Glu Pro Thr Lys Glu
                165                 170                 175

Lys Asp Ala Gly Gln Phe Val Cys Thr Ala Lys Asn Glu Ser Gly Lys
            180                 185                 190

Leu Thr Ala Thr Phe Thr Val Lys Phe Glu Val Pro Gln Gly Ala Pro
        195                 200                 205

Thr Phe Thr Arg Lys Pro Gln Ile Leu Gln Lys Thr Ser Asp Ser Gly
    210                 215                 220

Asp Pro Ala Ile Val Phe Asp Ile Gly Phe Gln Ala Asp Gln Asn Pro
225                 230                 235                 240

Gly Val Ile Trp Leu Asn Pro Lys Gly Lys Met Lys Glu Ser Ser
                245                 250                 255

Arg Ile Lys Phe Gly Leu Thr Pro Asp Gly Gly Ala Asn Thr Phe Thr
            260                 265                 270

Ala Gln Leu Glu Leu Lys Asn Tyr Lys Ala Lys Asp Ser Gly Thr Tyr
```

```
              275                 280                 285
Thr Cys Asn Ile Lys Asn Glu Ala Gly Glu Ala Asn Val Glu Leu Thr
    290                 295                 300
Leu Asn Ile Glu Gly Pro Leu Asp Glu Gly Ala Asp Asp Ala Ser Glu
305                 310                 315                 320
Ala
```

<210> SEQ ID NO 23
<211> LENGTH: 989
<212> TYPE: DNA
<213> ORGANISM: Dirofilaria immitis

<400> SEQUENCE: 23

```
ccagctgcag atcacgcttc gctagcatca tctgctcctt cgtctaaggg tccttcgata      60
ttcaatgtca attcgacgtt tgcttcacca gcttcattct tgatattgca ggtatatgta     120
ccactgtctt ttgctttata atttttcagt tctagctgag cagtgaacgt atttgcacca     180
ccatcaggtg ttaatccaaa ctttatacga cttgattcct tcattttttt gccttttgga     240
ttcaaccaaa taacccctgg gttctgatca gcttggaatc caatatcaaa gacaatggct     300
ggatcaccag aatctgatgt tttttgcaaa atctgtggtt tacgagtaaa ggttggagct     360
ccttgtggaa cttcaaattt aacagtaaaa gtggctgtta attttccaga ttcattttc      420
gctgtgcaaa caaattggcc cgcatctttt tctttcgtcg gctccttaat ttccagagca     480
gcataatacg tttgatttgc ctcttctatt agaacaattc tcactcgatc cgattcagct     540
acgatttctt caccctttg ccagacaaaa gtaggcatga gaattgactt tgctctgaat      600
tccataacca taacttgacc atcatcacga gatgatattt gtggcttttc gacaaatgtt    660
ggggcccaga agcctgtgag tttgagattg aaattggcat tcccctttcc gtgtggattt    720
acaatagcac atcggtaagc tccagcatca ctatcagcaa gatccttaat ttgtagaatg    780
gctgagtagg catcgtttcc tttattatcc agtcgaaaac tgaaccgctg gtcttgtttt    840
agttcggttg tatcataaaa ccatttaata tctggaactg gctgagcttc taaaaaacat    900
tccagttcca gtgacccatc atcgttttgt cgagctaccg gctgttgcgg gaatgaggt     960
gctttaccct ccggcattct cgagctcgg                                      989
```

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer
<223> OTHER INFORMATION: n = unknown at  3, 9, 12 and 21

<400> SEQUENCE: 24

```
ggnaargcnc cncayttycc ncarca                                           26
```

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer
<223> OTHER INFORMATION: n = unknown at 6, 15, 21, 24, 27, 30, 36, 39
      and 42

<400> SEQUENCE: 25
atytgnggyt tytcnacraa ngtnggngcn swraanccng tna    43

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ggaaagggga atgccaattt caatttcaat ctcaaactca caggcttctg g    51

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ccatcctaat acgactcact ataggga    27

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
ggtttaatta cccaagtttg ag    22

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ccagaagcct gtgagtttga gattgaaatt ggcattcccc tttcc    45

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
ccgagctcga gaatgccgga gggtaaagca cctcat    36

<210> SEQ ID NO 31
<211> LENGTH: 35
<212> TYPE: DNA

-continued

```
<213> ORGANISM: Artificial Sequence
<220> FEATURE:
<223> OTHER INFORMATION: Description of Artificial Sequence:  Synthetic
      Primer

<400> SEQUENCE: 31
ccagctgcag atcacgcttc gctagcatca tctgc                                35
```

PARASITIC HELMINTH DIAG2 PROTEINS AND USES THEREOF

This application is a Divisional application of co-pending application Ser. No. 09/361,434, filed Jul. 27, 1999, U.S. Pat. No. 6,136,963, entitled "PARASITC HELMINTH DiAg2 NUCLEIC ACID MOLECULES, AND USES THEREOF", which is incorporated herein by this reference in its entirety.

FIELD OF THE INVENTION

The present invention relates to parasitic helminth Antigen-2 (DiAg2) nucleic acid molecules, proteins encoded by such nucleic acid molecules and antibodies raised against such proteins. The present invention also includes therapeutic compositions comprising such nucleic acid molecules, proteins, and/or antibodies, as well as their use to protect animals from diseases caused by parasitic helminths.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths however there is yet to be a commercially available vaccine developed for any parasitic helminth.

As an example of the complexity of parasitic helminths, the life cycle of *Dirofilaria immitis*, the falariid nematode that causes heartworm, includes a variety of life forms, each of which presents different targets, and challenges, for immunization. In a mosquito, *D. immitis* microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog. In particular, heartworm is a major problem in dogs, which typically do not develop immunity upon infection (i.e., dogs can become reinfected even after being cured by chemotherapy). In addition, heartworm infection has been reported in cats, ferrets, and humans.

As such, there remains a need to identify efficacious compositions that protect animals against diseases caused by parasitic helminths such as *D. immitis*. Such compositions would preferably also protect animals from infection by such helminths.

SUMMARY OF THE INVENTION

The present invention relates to a novel product and a process to protect animals against parasitic helminth infection (e.g., prevent and/or treat such an infection). According to the present invention there are provided a parasitic helminth DiAg2 protein (e.g. a Dirofilaria DiAg2 protein) and a mimetope thereof; a parasitic helminth DiAg2 nucleic acid molecule, including those that encode such a protein; and an antibody raised against such a DiAg2 protein (i.e., an anti-parasitic helminth DiAg2 antibody).

The present invention also includes methods to obtain and/or identify such a protein, nucleic acid molecule, and antibody. Also included in the present invention is a therapeutic composition comprising such a protein, nucleic acid molecule, and/or antibody, as well as use of such a therapeutic composition to protect animals from diseases caused by parasitic helminths.

A preferred parasitic helminth DiAg2 nucleic acid molecule of the present invention includes an isolated nucleic acid molecule selected from the group consisting of: (a) a nucleic acid molecule comprising a nucleic acid sequence selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and SEQ ID NO:23; and (b) a nucleic acid molecule comprising an at least 24 consecutive nucleotide portion identical in sequence to a consecutive 24 nucleotide portion of a sequence as set forth in (a).

A preferred parasitic helminth DiAg2 nucleic acid molecule of the present invention includes an isolated filariid nematode nucleic acid molecule that hybridizes to a nucleic acid sequence selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23, under conditions comprising (a) hybridizing in a solution comprising 1×SSC and 0% formamide, at a temperature of about 37° C. and (b) washing in a solution comprising 1×SSC and 0% formamide, at a temperature of about 49° C.

The present invention also relates to a nucleic acid molecule, a recombinant molecule, a recombinant virus and a recombinant cell that includes an isolated DiAg2 nucleic acid molecule of the present invention. Also included are methods to produce such a recombinant molecule, recombinant molecule, recombinant virus and recombinant cell.

Another embodiment of the present invention includes a parasitic helminth DiAg2 protein. A preferred parasitic helminth DiAg2 protein includes an isolated protein selected from the group consisting of: (a) a protein comprising an amino acid sequence selected from the group consisting of SEQ ID NO:1, SEQ ID NO:2, SEQ ID NO:4, SEQ ID NO:7, SEQ ID NO:12, SEQ ID NO:17, and SEQ ID NO:22; (b) a protein comprising an at least 30 consecutive amino acid portion identical in sequence to a consecutive 30 amino acid portion of a sequence selected from the group consisting of SEQ ID NO:4, SEQ ID NO:7, SEQ ID NO:12, SEQ ID NO:17, and SEQ ID NO:22; (c) a protein comprising a fragment of a protein as set forth in (a).

A preferred parasitic helminth DiAg2 protein includes an isolated filariid nematode protein comprising an amino acid sequence that is at least about 70% identical to an amino acid sequence selected from the group consisting of SEQ ID NO:1, SEQ ID NO:2, SEQ ID NO:4, SEQ ID NO:7, SEQ ID NO:12, SEQ ID NO:17, and/or SEQ ID NO:22 or fragments thereof.

A preferred parasitic helminth DiAg2 protein includes a Dirofilaria DiAg2 protein. More preferred DiAg2 proteins include *Dirofilaria immitis* DiAg2 proteins. A particularly preferred *D. immitis* DiAg2 protein comprises amino acid sequence SEQ ID NO:1, SEQ ID NO:2, SEQ ID NO:4, SEQ ID NO:7, SEQ ID NO:12, SEQ ID NO:17, and/or SEQ ID NO:22. The present invention further relates to isolated antibodies that selectively bind to parasitic helminth DiAg2 proteins of the present invention, or to a mimetope thereof.

Yet another embodiment of the present invention is a therapeutic composition that is capable of protecting an animal from disease caused by a parasitic helminth. Such a therapeutic composition includes one or more of the following protective compounds: a parasitic helminth DiAg2 protein or a mimetope thereof; an isolated parasitic helminth DiAg2 nucleic acid molecule; an isolated antibody that selectively binds to a parasitic helminth DiAg2 protein; and/or a compound capable of inhibiting DiAg2 function identified by its ability to inhibit parasitic helminth DiAg2 function. A preferred therapeutic composition of the present invention also includes an excipient, an adjuvant and/or a carrier. Preferred DiAg2 nucleic acid molecule therapeutic compositions of the present invention include genetic vaccines, recombinant virus vaccines and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated parasitic helminth Antigen-2 (DiAg2) proteins, isolated parasitic helminth DiAg2 nucleic acid molecules, isolated antibodies directed against parasitic helminth DiAg2 proteins, and compounds able to inhibit parasitic helminth DiAg2 function (i.e., inhibitory compounds). *D. immitis* extracts were shown by Western blot analysis to contain a 39 kDa protein that reacted with serum isolated from immune dogs (i.e., immune dog serum), see PCT publication WO 92/13560 by Grieve et al., published Aug. 20, 1992, which is incorporated herein by reference in its entirety. Initial attempts to isolate a nucleic acid sequence encoding a 39 kDa protein as described by Grieve et al. resulted in the isolation of a cDNA encoding a 39 kDa protein, see U.S. patent application Ser. Nos. 08/473,034 and 08/487,031, each of which is incorporated herein by reference in its entirety. The 39 kD recombinant protein expressed by this cDNA, however, was shown not to be recognized by immune dog serum. The present application includes the surprising discovery of a *D. immitis* 39 kDa protein which is different from the protein described in U.S. patent application Ser. Nos. 08/473,034 and 08/487,031 and which does react with (i.e., binds to) immune dog serum.

As used herein, the terms isolated parasitic helminth DiAg2 proteins and isolated parasitic helminth DiAg2 nucleic acid molecules refer to DiAg2 proteins and DiAg2 nucleic acid molecules derived from parasitic helminths; as such the proteins and nucleic acid molecules can be isolated from an organism or prepared recombinantly or synthetically. Parasitic helminth DiAg2 nucleic acid molecules of known length are denoted "nDiAg2$_\#$" (for example nDiAg2$_{1106}$) wherein "#" refers to the number of nucleotides in that molecule, and DiAg2 proteins of known length are denoted "PDiAg2$_\#$" (for example PDiAg2$_{321}$) wherein "#" refers to the number of amino acid residues in that molecule. The proteins and nucleic acid molecules of the present invention can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from parasitic helminth diseases as well as in other applications, such as those disclosed below.

One embodiment of the present invention is an isolated protein that includes a parasitic helminth DiAg2 protein. It is to be noted that the term "a" or "an" entity refers to one or more of that entity; for example, a protein, a nucleic acid molecule, an antibody, an inhibitor, a compound or a therapeutic composition refers to "one or more" or "at least one" protein, nucleic acid molecule, antibody, inhibitor, compound or therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated parasitic helminth DiAg2 protein of the present invention can be a fill-length protein or any homologue of such a protein. An isolated protein of the present invention, including a homologue, can be identified in a straight-forward manner by the protein's ability to elicit an immune response against a parasitic helminth DiAg2 protein, and preferably against a protein having SEQ ID NO:3, SEQ ID NO:6, SEQ ID NO:9, SEQ ID NO:11, SEQ ID NO:14, SEQ ID NO:16, SEQ ID NO:19 and/or SEQ ID NO:21, or by the protein's DiAg2 activity. Examples of parasitic helminth DiAg2 homologue proteins include parasitic helminth DiAg2 proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a parasitic helminth DiAg2 protein, and/or of binding to an antibody directed against a parasitic helminth DiAg2 protein. For example, when a homologue is administered to an animal as an immunogen, using techniques known to those skilled in the art, the animal will produce an immune response against at least one epitope of a natural parasitic helminth DiAg2 protein. The ability of a protein to effect an immune response can be measured using techniques known to those skilled in the art. Methods to determine binding between proteins and antibodies are also know to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids. In one embodiment of the present invention a parasitic helminth homologue protein has DiAg2 activity.

Parasitic helminth DiAg2 homologue proteins can be the result of natural allelic variation or natural mutation. Parasitic helminth DiAg2 protein homologues of the present invention can also be produced using techniques known in the art including, but not limited to, direct modifications to the protein or modifications to the gene or cDNA encoding the protein using, for example, classic or recombinant DNA techniques to effect random or targeted mutagenesis.

Parasitic helminth DiAg2 proteins of the present invention are encoded by parasitic helminth DiAg2 nucleic acid molecules. As used herein, a parasitic helminth DiAg2 nucleic acid molecule includes nucleic acid sequences related to a natural parasitic helminth DiAg2 gene, and, preferably, to a Dirofilaria DiAg2 gene and more preferably to a *Dirofilaria immitis* DiAg2 gene. Other examples of parasitic helminths from which to isolate proteins, genes and nucleic acid molecules are disclosed herein. As used herein, a parasitic helminth DiAg2 gene includes all regions such as regulatory regions that control production of the parasitic helminth DiAg2 protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a *D. immitis* DiAg2 gene that includes the nucleic acid sequence SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23, as well as the complements of any of these nucleic acid sequences. These nucleic acid sequences are further described herein. For example, nucleic acid sequence SEQ ID NO:21 represents the deduced sequence of the coding strand of a cDNA (complementary DNA) denoted herein as *D. immitis* DiAg2 nucleic acid molecule nDiAg2$_{989}$, the production of which is disclosed in the Examples. Nucleic acid molecule nDiAg2$_{989}$ comprises an apparent fill-length coding region. The complement of SEQ ID NO:21 (represented herein by SEQ ID NO:23) refers to the nucleic acid sequence of the strand complementary to the strand having SEQ ID NO:21, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:21 (as well as other nucleic acid and protein sequences presented herein) represents an apparent nucleic acid sequence of the nucleic acid molecule encoding a DiAg2 protein of the present invention.

In another embodiment, a DiAg2 gene or nucleic acid molecule can be an allelic variant that includes a similar but not identical sequence to SEQ ID NO:21, SEQ ID NO:23, or any other *D. immitis* nucleic acid sequence cited herein. For example, an allelic variant of a DiAg2 gene including SEQ ID NO:21 and SEQ ID NO:23, is a gene that occurs at essentially the same locus (or loci) in the genome as the gene including SEQ ID NO:21 and SEQ ID NO:23, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given parasitic helminth such as Dirofilaria, since the respective genomes are diploid, and sexual reproduction will result in the reassortment of alleles.

In one embodiment of the present invention, an isolated DiAg2 protein is encoded by a nucleic acid molecule that hybridizes under stringent hybridization conditions to a gene encoding a parasitic helminth DiAg2 protein. The minimal size of a DiAg2 protein of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the parasitic helminth DiAg2 nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a parasitic helminth DiAg2 protein is typically at least about 12 to about 15 nucleotides in length if the nucleic acid molecule is GC-rich and at least about 15 to about 17 bases in length if it is AT-rich. The minimal size of a nucleic acid molecule used to encode a DiAg2 protein homologue of the present invention is from about 12 to about 18 nucleotides in length. Thus, the minimal size of a DiAg2 protein homologue of the present invention is from about 4 to about 6 amino acids in length. There is no limit, other than a practical limit, on the maximal size of a nucleic acid molecule encoding a parasitic helminth DiAg2 protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\%G+C) - 500/n - 0.61(\%\text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *Dirofilaria immitis* nucleic acid molecule of about 150 bp in length, the following conditions could preferably be used. The average G+C content of *D. immitis* DNA is about 35%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 79° C.:

$$81.5° C. + 16.6 \log(0.15M) + (0.41 \times 35) - (500/150) - (0.61 \times 0) = 79° C.$$

Thus, to achieve hybridization with nucleic acid molecules having about 30% base-pair mismatch, hybridization washes would be carried out at a temperature of about 49° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 49° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, PC/GENE™ DNA Sequence Analysis System, hereinafter "PC/GENE", (available from Intelligenetics, Inc./ Mountainview, Calif.); GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using default parameters of the PC/GENE™ computer program, i.e. an open gap cost of 10 and a unit gap cost of 10.

A preferred parasitic helminth DiAg2 protein includes an isolated protein selected from the group consisting of: (a) a protein comprising an amino acid sequence selected from the group consisting of SEQ ID NO:1, SEQ ID NO:2, SEQ ID NO:4, SEQ ID NO:7, SEQ ID NO:12, SEQ ID NO:17, and SEQ ID NO:22; (b) a protein comprising an at least 30 consecutive amino acid portion identical in sequence to a consecutive 30 amino acid portion of a sequence selected from the group consisting of SEQ ID NO:4, SEQ ID NO:7, SEQ ID NO:12, SEQ ID NO:17, and SEQ ID NO:22; (c) a protein comprising a fragment of a protein as set forth in (a).

One embodiment of the present invention includes parasitic helminth DiAg2 proteins. A preferred parasitic helminth DiAg2 protein includes a protein encoded by a nucleic acid molecule which is less than about 50 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:5, SEQ ID NO:8, SEQ ID NO:10, SEQ ID NO:13, SEQ ID NO:15, SEQ ID NO:18, SEQ ID NO:20, and/or SEQ ID NO:23.

Another preferred parasitic helminth DiAg2 protein of the present invention includes a protein encoded by a nucleic acid molecule which is at least about 50 to at least about 150 nucleotides in length and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:5, SEQ ID NO:8, SEQ ID NO:10, SEQ IDNO:13, SEQ ID NO:15, SEQ ID NO:18, SEQ ID NO:20, and/or SEQ ID NO:23.

Another preferred parasitic helminth DiAg2 protein of the present invention includes a protein encoded by a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:5, SEQ ID NO:8, SEQ ID NO:10, SEQ ID NO:13, SEQ ID NO:15, SEQ ID NO:18, SEQ ID NO:20, and/or SEQ ID NO:23.

Another embodiment of the present invention includes a parasitic helminth DiAg2 protein encoded by a nucleic acid molecule which hybridizes to an isolated nucleic acid molecule selected from the group consisting of SEQ ID NO:5, SEQ ID NO:8, SEQ ID NO:10, SEQ ID NO:13, SEQ ID NO:15, SEQ ID NO:18, SEQ ID NO:20, and/or SEQ ID NO:23, under conditions comprising (a) hybridizing in a solution comprising 1×SSC and 0% formamide, at a temperature of about 37° C. and (b) washing in a solution comprising 1×SSC and 0% formamide, at a temperature of about 49° C.

Yet another preferred parasitic helminth DiAg2 protein of the present invention includes a protein encoded by a nucleic acid molecule which is preferably about 70% identical, more preferably about 75% identical, more preferably about 80% identical, more preferably about 85% identical, more preferably about 90% identical and even more preferably about 95% identical to a nucleic acid molecule having the nucleic acid sequence SEQ ID NO:3, SEQ ID NO:6, SEQ ID NO:9, SEQ ID NO:11, SEQ ID NO:14, SEQ ID NO:16, SEQ ID NO:19 and/or SEQ ID NO:21. Percent identity as used herein is determined using the program PC/GENE™ with default parameters. Also preferred are proteins encoded fragments of such nucleic acid molecules.

Preferred parasitic helminth proteins of the present invention include proteins having the amino acid sequence SEQ ID NO:1, SEQ ID NO:2, SEQ ID NO:4, SEQ ID NO:7, SEQ ID NO:12, SEQ ID NO:17, and/or SEQ ID NO:22, including, but not limited to, the proteins consisting of amino acid sequence SEQ ID NO:1, SEQ ID NO:2, SEQ ID NO:4, SEQ ID NO:7, SEQ ID NO:12, SEQ ID NO:17, and/or SEQ ID NO:22, fusion proteins and multivalent proteins. Preferred parasitic helminth proteins of the present invention include proteins comprising homologues of a protein having the amino acid sequence SEQ ID NO:1, SEQ ID NO:2, SEQ ID NO:4, SEQ ID NO:7, SEQ ID NO:12, SEQ ID NO:17, and/or SEQ ID NO:22 wherein such a homologue comprises at least one epitope that elicits an immune response against a protein having an amino acid sequence SEQ ID NO:1, SEQ ID NO:2, SEQ ID NO:4, SEQ ID NO:7, SEQ ID NO:12, SEQ ID NO:17, and/or SEQ ID NO:22. Also preferred are proteins having sequences described herein from which the initiating methionine has been removed. Likewise, also preferred are proteins encoded by nucleic acid molecules having nucleic acid sequence SEQ ID NO:3, SEQ ID NO:6, SEQ ID NO:9, SEQ ID NO:11, SEQ ID NO:14, SEQ ID NO:16, SEQ ID NO:19 and/or SEQ ID NO:21, or by homologues thereof.

A preferred isolated protein of the present invention is a protein encoded by at least one of the following nucleic acid molecules:nDiAg2$_{332}$, nDiAg2$_{775}$, nDiAg2$_{699}$, nDiAg2$_{376}$, nDiA2$_{312}$, nDiAg2$_{1106}$, nDiAg2$_{963}$, and/or nDiAg2$_{989}$, or allelic variants of any of these nucleic acid molecules. Another preferred isolated protein is encoded by a nucleic acid molecule having nucleic acid sequence SEQ ID NO:3, SEQ ID NO:6, SEQ ID NO:9, SEQ ID NO:11, SEQ ID NO:14, SEQ ID NO:16, SEQ ID NO:19 and/or SEQ ID NO:21; or a protein encoded by an allelic variant of any of these listed nucleic acid molecules.

Translation of SEQ ID NO:3, the coding strand of nDiAg2$_{332}$, yields a protein of about 110 amino acids, denoted herein as PDiAg2$_{110}$, the amino acid sequence of which is presented in SEQ ID NO:4, assuming a first in-frame codon extending from nucleotide 1 to nucleotide 3 of SEQ ID NO:3 and a last in-frame codon extending from nucleotide 328 to nucleotide 330 of SEQ ID NO:3.

Translation of SEQ ID NO:6, the coding strand of nDiAg2$_{775}$, yields a protein of about 232 amino acids, denoted herein as PDiAg2$_{232}$, the amino acid sequence of which is presented in SEQ ID NO:7, assuming a first in-frame codon extending from nucleotide 1 to nucleotide 3 of SEQ ID NO:6 and a last in-frame codon extending from nucleotide 694 to nucleotide 696 of SEQ ID NO:6.

Translation of SEQ ID NO:11, the coding strand of nDiAg2$_{376}$, yields a protein of about 104 amino acids, denoted herein as PDiAg2$_{104}$, the amino acid sequence of which is presented in SEQ ID NO:12, assuming a first in-frame codon extending from nucleotide 65 to nucleotide 67 of SEQ ID NO:11 and a last in-frame codon extending from nucleotide 374 to nucleotide 376 of SEQ ID NO:11.

Translation of SEQ ID NO:16, the coding strand of nDiAg2$_{1106}$, yields a protein of about 321 amino acids, denoted herein as PDiAg2$_{321}$, the amino acid sequence of which is presented in SEQ ID NO:17, assuming a first in-frame codon extending from nucleotide 65 to nucleotide 67 of SEQ ID NO:16 and a last in-frame codon extending from nucleotide 1025 to nucleotide 1027 of SEQ ID NO:16.

Translation of SEQ ID NO:21, the coding strand of nDiAg2$_{989}$, yields a protein of about 321 amino acids, denoted herein as PDiAg2$_{321}$, the amino acid sequence of which is presented in SEQ ID NO:22, assuming a first in-frame codon extending from nucleotide 13 to nucleotide 16 of SEQ ID NO:21 and a last in-frame codon extending from nucleotide 973 to nucleotide 975 of SEQ ID NO:21.

Preferred DiAg2 proteins of the present invention include proteins that are at least about 70%, more preferably at least about 75%, more preferably at least about 80%, more preferably at least about 85%, more preferably at least about 90%, more preferably at least about 92%, more preferably at least about 95%, even more preferably at least about 98%, and even more preferably about 100% identical to PDiAg2$_{321}$. More preferred are DiAg2 proteins comprising PDiAg2$_{110}$, PDiAg2$_{232}$, PDiAg2$_{104}$, and/or PDiAg2$_{321}$; and proteins encoded by allelic variants of nucleic acid molecules encoding proteins PDiAg2$_{110}$, PDiAg2$_{232}$, PDiAg2$_{104}$, and/or PDiAg2$_{321}$. Percent identity as used herein is determined using the program PC/GENE™ with default parameters.

As such, preferred DiAg2 proteins of the present invention include proteins having amino acid sequences that are at least about 70%, more preferably at least about 75%, more preferably at least about 80%, more preferably at least about 85%, more preferably at least about 90%, more preferably at least about 92%, more preferably at least about 95%, even more preferably at least about 98%, and even more preferably about 100% identical to amino acid sequence SEQ ID NO:1, SEQ ID NO:2, SEQ ID NO:4, SEQ ID NO:7, SEQ ID NO:12, SEQ ID NO:17, and/or SEQ ID NO:22. Also preferred are fragments of any of such proteins. Percent identity as used herein is determined using the program PC/GENE™ with default parameters. More preferred are DiAg2 proteins comprising amino acid sequences SEQ ID NO:1, SEQ ID NO:2, SEQ ID NO:4, SEQ ID NO:7, SEQ ID NO:12, SEQ ID NO:17, and/or SEQ ID NO:22; and DiAg2 proteins encoded by allelic variants of nucleic acid molecules encoding DiAg2 proteins having amino acid sequences SEQ ID NO:1, SEQ ID NO:2, SEQ ID NO:4, SEQ ID NO:7, SEQ ID NO:12, SEQ ID NO:17, and/or SEQ ID NO:22.

In one embodiment, a preferred DiAg2 protein comprises an amino acid sequence of at least about 5 amino acids in length, preferably at least about 10 amino acids in length, preferably at least about 15 amino acids in length, preferably at least about 20 amino acids in length, preferably at least about 25 amino acids in length, preferably at least about 35 amino acids in length, preferably at least about 50 amino acids in length, preferably at least about 100 amino acids in length, preferably at least about 200 amino acids in length, preferably at least about 250 amino acids in length, preferably at least about 300 amino acids in length, and preferably at least about 320 amino acids in length. Within this embodiment, a preferred *D. immitis* DiAg2 protein of the present invention has an amino acid sequence comprising at least a portion of SEQ ID NO:17. In another embodiment, a preferred parasitic helminth DiAg2 protein comprises a full-length protein, i.e., a protein encoded by a full-length coding region with or without an initiating methionine residue.

Preferred DiAg2 proteins of the present invention include proteins encoded by nucleic acid molecules comprising at least a portion of nDiAg2$_{332}$, nDiAg2$_{775}$, nDiAg2$_{699}$, nDiAg2$_{376}$, nDiAg2$_{312}$, nDiAg2$_{1106}$, nDiAg2$_{963}$, and/or nDiAg2$_{989}$, as well as DiAg2 proteins encoded by allelic variants of such nucleic acid molecules.

Also preferred are DiAg2 proteins encoded by nucleic acid molecules having nucleic acid sequences comprising at least a portion of SEQ ID NO:3, SEQ ID NO:6, SEQ ID NO:9, SEQ ID NO:11, SEQ ID NO:14, SEQ ID NO:16, SEQ ID NO:19 and/or SEQ ID NO:21, as well as allelic variants of these nucleic acid molecules.

In another embodiment, a preferred *D. immitis* DiAg2 protein of the present invention is encoded by a nucleic acid molecule comprising at least about 15 nucleotides, preferably at least about 20 nucleotides, preferably at least about 25 nucleotides, preferably at least about 35 nucleotides, at least about 50 nucleotides, preferably at least about 100 nucleotides, preferably at least about 250 nucleotides, preferably at least about 300 nucleotides, preferably at least about 350 nucleotides, preferably at least about 500 nucleotides, preferably at least about 750 nucleotides, preferably at least about 900 nucleotides, preferably at least about 950 nucleotides, preferably at least about 1000 nucleotides, and preferably at least about 1100 nucleotides. Within this embodiment is a DiAg2 protein encoded by at least a portion nDiAg2$_{1106}$ or by an allelic variant of this nucleic acid molecule. In yet another embodiment, a preferred parasitic helminth DiAg2 protein of the present invention is encoded by a nucleic acid molecule comprising an apparently full-length DiAg2 coding region, i.e., a nucleic acid molecule encoding an apparently fill-length DiAg2 protein, with or without an initiating methionine amino acid residue.

A preferred parasitic helminth DiAg2 protein of the present invention is a compound that when administered to an animal in an effective manner, is capable of protecting that animal from disease caused by a parasitic helminth. In accordance with the present invention, the ability of a DiAg2 protein of the present invention to protect an animal from disease by a parasitic helminth refers to the ability of that protein to, for example, treat, ameliorate and/or prevent disease caused by parasitic helminths. In one embodiment, a parasitic helminth DiAg2 protein of the present invention can elicit an immune response (including a humoral and/or cellular immune response) against a parasitic helminth.

Suitable parasitic helminths to target include any parasitic helminth that is essentially incapable of causing disease in an animal administered a parasitic helminth DiAg2 protein of the present invention. As such, parasitic helminths to target includes any parasitic helminth that produces a protein having one or more epitopes that can be targeted by a humoral and/or cellular immune response against a parasitic helminth DiAg2 protein of the present invention and/or that can be targeted by an inhibitory compound that otherwise inhibits parasitic helminth DiAg2 function (e.g., a compound that binds to parasitic helminth DiAg2 thereby blocking parasitic helminth development and/or migration regulatory pathways), thereby resulting in the decreased ability of the parasite to cause disease in an animal. Preferred parasitic helminths to target include nematodes, cestodes, and trematodes, with nematodes being preferred. Preferred parasitic helminths to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *Dirofilaria immitis, Onchocerca volvulus, Brugia malayi* and *Brugia pahangi* being even more preferred.

One embodiment of a parasitic helminth DiAg2 protein of the present invention is a fusion protein that includes a parasitic helminth DiAg2 protein-containing domain attached to one or more fusion segments. Suitable fusion segments for use with the present invention include, but are not limited to, segments that can: enhance a protein's stability; act as an immunopotentiator to enhance an immune response against a parasitic helminth DiAg2 protein; and/or assist in purification of a parasitic helminth DiAg2 protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the parasitic helminth DiAg2-containing domain of the protein and can be susceptible to cleavage in order to enable straight-forward recovery of a parasitic helminth DiAg2 protein. Fusion proteins are preferably produced by culturing a recombinant cell transformed with a fusion nucleic acid molecule that encodes a protein including the fusion segment attached to either the carboxyl and/or amino terminal end of a DiAg2-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

In another embodiment, a parasitic helminth DiAg2 protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, a parasitic helminth DiAg2 protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococct's, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a parasitic helminth DiAg2 protein of the present invention is attached to one or more additional compounds protective against diseases caused by parasitic helminths, for example heartworm disease or elephantiasis. In another embodiment, one or more protective compounds, such as those listed above, can be included in a multivalent vaccine comprising a parasitic helminth DiAg2 protein of the present invention and one or more other protective molecules as separate compounds.

The present invention also includes mimetopes of parasitic helminth DiAg2 proteins of the present invention. As used herein, a mimetope of a parasitic helminth DiAg2 protein of the present invention refers to any compound that is able to mimic the activity of such a DiAg2 protein, often because the mimetope has a structure that mimics the particular DiAg2 protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a parasitic helminth DiAg2 nucleic acid molecule. The identifying characteristics of such nucleic acid molecules are heretofore described. A nucleic acid molecule of the present invention can include an isolated natural parasitic helminth DiAg2 gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a DiAg2 nucleic acid molecule of the present invention is from about 12 to about 18 nucleotides in length. Suitable and preferred parasitic helminths from which to isolate nucleic acid molecules of the present invention are disclosed herein. Preferred DiAg2 nucleic acid molecules include Dirofilaria, Brugia, and Onchocerca nucleic acid molecules. Particularly preferred DiAg2 nucleic acid molecules include *D. immitis*, *B. malayi*, *B. pahangi* and *O. volvulus* DiAg2 nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated parasitic helminth DiAg2 nucleic acid molecule of the present invention, can be isolated from its natural source or produced using recombinant DNA technology (e.g., polymerase chain reaction (PCR) amplification or cloning) or chemical synthesis. Isolated parasitic helminth DiAg2 nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a DiAg2 protein of the present invention.

A parasitic helminth DiAg2 nucleic acid molecule homologue can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with a parasitic helminth DiAg2 nucleic acid molecule or by screening for the function of a protein encoded by the nucleic acid molecule (e.g., ability to elicit an immune response against at least one epitope of a parasitic helminth DiAg2 protein or ability of the protein to bind to serum from an immune dog).

An isolated nucleic acid molecule of the present invention can include a nucleic acid sequence that encodes at least one parasitic helminth DiAg2 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth DiAg2 protein or being capable of hybridizing to a nucleic acid molecule or nucleic acid sequence.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., a DiAg2 protein of the present invention), the nucleic acid molecule being delivered to the animal, for example, by direct injection (i.e, as a genetic vaccine) or in a vehicle such as a recombinant virus vaccine or a recombinant cell vaccine.

A preferred parasitic helminth DiAg2 nucleic acid molecule of the present invention includes an isolated nucleic acid molecule selected from the group consisting of: (a) a nucleic acid molecule comprising a nucleic acid sequence selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and SEQ ID NO:23; and (b) a nucleic acid molecule comprising an at least 24 consecutive nucleotide portion identical in sequence to a consecutive 24 nucleotide portion of a sequence as set forth in (a).

In one embodiment of the present invention, a preferred parasitic helminth DiAg2 nucleic acid molecule includes an isolated nucleic acid molecule which is less than about 50 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23.

In one embodiment of the present invention, a preferred parasitic helminth DiAg2 nucleic acid molecule includes an isolated nucleic acid molecule which is at least about 50 nucleotides and less than about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:5, SEQ ID NO:16, SEQ ID NO:18, SEQ ID NO:19, SEQ ID NO:20, SEQ ID NO:21, and/or SEQ ID NO:23.

Another preferred parasitic helminth DiAg2 nucleic acid molecule of the present invention includes a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23.

Another embodiment of the present invention includes a nucleic acid molecule that hybridizes to an isolated nucleic acid molecule selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23, under conditions comprising (a) hybridizing in a solution comprising 1×SSC and 0% formamide, at a temperature of about 37° C. and (b) washing in a solution comprising 1×SSC and 0% formamide, at a temperature of about 49° C.

In one embodiment, a preferred parasitic helminth DiAg2 nucleic acid molecule of the present invention includes a nucleic acid molecule comprising a nucleic acid sequence that is preferably at least about 70%, more preferably at least about 75%, more preferably at least about 80%, more preferably at least about 85%, more preferably at least about 90%, more preferably at least about 95%, and even more preferably at least about 100% identical to a nucleic acid sequence selected from the group consisting of SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23. Also preferred are fragments of such a nucleic acid molecule. A particularly preferred parasitic helminth nucleic acid molecule includes a Dirofilaria DiAg2 nucleic acid molecule, preferably a *Dirofilaria immitis* (*D. immitis*) DiAg2 nucleic acid molecule. A *D. immitis* DiAg2 nucleic acid molecule preferably includes nucleic acid sequence SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23. Percent identity as used herein is determined using the program PC/GENE™ with default parameters.

One embodiment of the present invention is a nucleic acid molecule comprising all or part of nucleic acid molecules nDiAg2$_{332}$, nDiAg2$_{775}$, nDiAg2$_{699}$, nDiAg2$_{376}$, nDiAg2$_{312}$, nDiAg2$_{1106}$, nDiAg2$_{963}$, and/or nDiAg2$_{989}$, or allelic variants of these nucleic acid molecules. As such, a preferred nucleic acid molecule of the present invention includes at least a portion of nucleic acid sequence SEQ ID NO:3, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, and/or SEQ ID NO:23, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:1, SEQ ID NO:2, SEQ ID NO:4, SEQ ID NO:7, SEQ ID NO:12, SEQ ID NO:17, and/or SEQ ID NO:22. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, a DiAg2 nucleic acid molecule of the present invention encodes a protein that is at least about 70%, more preferably at least about 75%, more preferably at least about 80%, more preferably at least about 85%, more preferably at least about 90%, more preferably at least about 92%, more preferably at least about 95%, even more preferably at least about 98%, and even more preferably about 100% identical to PDiAg2$_{321}$ or a fragment thereof. Even more preferred is a nucleic acid molecule encoding PDiAg2$_{110}$, PDiAg2$_{232}$, PDiAg2$_{104}$, and/or PDiAg2$_{321}$, and/or an allelic variant of such a nucleic acid molecule. Percent identity as used herein is determined using the program PC/GENE™ with default parameters.

A preferred DiAg2 nucleic acid molecule of the present invention encodes a protein having an amino acid sequence that is at least about 70%, more preferably at least about 75%, more preferably at least about 80%, more preferably at least about 85%, more preferably at least about 90%, more preferably at least about 92%, more preferably at least about 95%, even more preferably at least about 98%, and even more preferably about 100% identical to SEQ ID NO:1, SEQ ID NO:2, SEQ ID NO:4, SEQ ID NO:7, SEQ ID NO:12, SEQ ID NO:17, and/or SEQ ID NO:22 or a fragment of any of such amino acid sequences. Percent identity as used herein is determined using the program PC/GENE™ with default parameters.

The present invention also includes a DiAg2 nucleic acid molecule encoding a protein having at least a portion of SEQ ID NO:1, SEQ ID NO:2, SEQ ID NO:4, SEQ ID NO:7, SEQ ID NO:12, SEQ ID NO:17, and/or SEQ ID NO:22, as well as allelic variants of a DiAg2 nucleic acid molecule encoding a protein having these sequences, including nucleic acid molecules that have been modified to accommodate codon usage properties of the cells in which such nucleic acid molecules are to be expressed.

In another embodiment, a preferred parasitic helminth DiAg2 nucleic acid molecule encodes a DiAg2 protein comprising at least about 5 amino acids in length, preferably at least about 10 amino acids in length, preferably at least about 15 amino acids in length, preferably at least about 20 amino acids in length, preferably at least about 25 amino acids in length, preferably at least about 35 amino acids in length, preferably at least about 50 amino acids in length, preferably at least about 100 amino acids in length, preferably at least about 200 amino acids in length, preferably at least about 250 amino acids in length, preferably at least about 300 amino acids in length, and preferably at least about 310 amino acids in length.

In yet another embodiment, a preferred parasitic helminth DiAg2 nucleic acid molecule of the present invention comprises an apparently full-length DiAg2 coding region, i.e., the preferred nucleic acid molecule encodes an apparently full-length DiAg2 protein with or without an initiating methionine.

Knowing the nucleic acid sequences of certain parasitic helminth DiAg2 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other parasitic helminth DiAg2 nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria L4 or adult cDNA libraries as well as genomic DNA libraries. Similarly, preferred DNA sources from which to amplify nucleic acid molecules include Dirofilaria L4 or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising Dirofilaria DiAg2 nucleic acid molecules or other parasitic helminth DiAg2 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides. The present invention includes oligonucleotides that can be used as, for example, probes to identify nucleic acid molecules, primers to produce nucleic acid molecules, or therapeutic reagents to inhibit parasitic helminth DiAg2 protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth DiAg2 nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, Caulobacter, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as *D immitis* transcription control sequences.

Suitable and preferred nucleic acid molecules to include in recombinant vectors of the present invention are as disclosed herein. Particularly preferred nucleic acid molecules to include in recombinant vectors, and particularly in recombinant molecules, include $nDiAg2_{332}$, $nDiAg2_{775}$, $nDiAg2_{699}$, $nDiAg2_{376}$, $nDiAg2_{312}$, $nDiAg2_{1106}$, $nDiAg2_{963}$, and/or $nDiAg2_{989}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, yeast alpha factor, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Dirofilaria nucleic acid molecules disclosed herein. Particularly preferred nucleic acid molecules with which to transform a cell include $nDiAg2_{332}$, nDiAg775, $nDiAg2_{699}$, $nDiAg2_{376}$, $nDiAg2_{312}$, $nDiAg2_{1106}$, $nDiAg2_{963}$, and/or $nDiAg2_{989}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing parasitic helminth DiAg2 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Caulobacter, Listena, Pichia, Hansenula, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_{\chi}3987$ and SR-11 $_{\phi}4072$*; Pichia pastoris, Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including parasitic helminth DiAg2 nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated parasitic helminth DiAg2 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a parasitic helminth DiAg2 protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic helminth DiAg2 protein of the present invention or a mimetope thereof (e.g., anti-Dirofilaria DiAg2 antibodies). As used herein, the term "selectively binds to" a DiAg2 protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-DiAg2 antibody of the present invention preferably selectively binds to a parasitic helminth DiAg2 protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce DiAg2 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. In one embodiment, therapeutic compositions of the present invention inhibit molting of larvae; i.e. reduce the ability of a larva to develop from one stage to the next, e.g. from L3 to L4. Therapeutic compositions of the present invention include at least one of the following protective compounds: an isolated parasitic helminth DiAg2 protein or a mimetope thereof, an isolated parasitic helminth DiAg2 nucleic acid molecule, an isolated antibody that selectively binds to a parasitic helminth DiAg2 protein, an inhibitor of DiAg2 function identified by its ability to bind to a parasitic helminth DiAg2 protein and thereby impede development and/or migration of the parasite, and a mixture thereof (i.e., combination of at least two of the compoumds). As used herein, a protective compound refers to a compound that, when administered to an animal in an effective manner, is able to treat, ameliorate, and/or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth DiAg2-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals, work animals and/or zoo animals. Preferred animals to protect against heartworm disease include dogs, cats, humans and ferrets, with dogs and cats being particularly preferred. A preferred animal to protect against disease caused by parasitic helminths, for example river blindness or elephantiasis, includes humans.

In one embodiment, a therapeutic composition of the present invention can be administered to the vector in which the parasitic helminth develops, such as to a mosquito in order to prevent the spread of heartworm. Such administration could be oral or by developing transgenic vectors capable of producing at least one therapeutic composition of the present invention. In another embodiment, an insect vector, such as a mosquito, can ingest therapeutic compositions present in the blood of a host that has been administered a therapeutic composition of the present invention.

In order to protect an animal from disease caused by a parasitic helminth, a therapeutic composition of the present invention is administered to the animal in an effective manner such that the composition is capable of protecting that animal from a disease caused by a parasitic helminth. Therapeutic compositions of the present invention can be administered to animals prior to infection in order to prevent infection (i.e., as a preventative vaccine) and/or can be administered to animals after infection in order to treat disease caused by the parasitic helminth (i.e., as a therapeutic vaccine).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunters Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising a DiAg2 nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of Dirofilaria DiAg2 proteins, nucleic acid molecules, antibodies and inhibitors of the present invention, to protect an animal from heartworm. For example, an isolated protein or mimetope thereof is administered in an amount and manner that elicits (i.e., stimulates) an immune response that is sufficient, upon interaction with a native DiAg2 protein, to protect the animal from the disease. Similarly, an antibody of the present invention, when administered to an animal in an effective manner, is administered in an amount so as to be present in the animal at a titer that is sufficient, upon interaction of that antibody with a native DiAg2 protein, to protect the animal from the disease, at least temporarily. Oligonucleotide nucleic acid molecules of the present invention can also be administered in an effective manner, thereby reducing expression of parasitic helminth DiAg2 proteins in order to interfere with development of parasitic helminths targeted in accordance with the present invention. It is particularly preferred to prevent L3 that are delivered to the animal by the mosquito intermediate host from migrating from the site of inoculation and/or maturing into adult worms. As such, preferred therapeutic compositions are those that are able to inhibit at least one step in the portion of the parasite's development cycle that includes L3, third molt, L4, fourth molt, immature adult prior to entering the circulatory system. In dogs, this portion of the development cycle is about 70 days. Particularly preferred therapeutic compositions include *D. immitis* DiAg2-based therapeutic compositions of the present invention. Such compositions include *D. immitis* DiAg2 nucleic acid molecules, *D. immitis* DiAg2 proteins and mimetopes thereof, anti-*D. immitis* DiAg2 antibodies, and inhibitors of *D. immitis* DiAg2 function. Therapeutic compositions are administered to animals in a manner effective to protect the animals from heartworm. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of parasitic helminth DiAg2 function, i.e., a compound capable of substantially interfering with the function of a parasitic helminth DiAg2 protein susceptible to inhibition. An inhibitor of DiAg2 function can be identified using parasitic helminth DiAg2 proteins of the present invention. A preferred inhibitor of DiAg2 function is a compound capable of substantially interfering with the function of a parasitic helminth DiAg2 protein and which does not substantially interfere with host animal DiAg2 activity. As used herein, a compound that does not substantially inhibit host animal DiAg2 activity is one that, when administered to a host animal, the host animal shows no significant adverse effects attributable to the compound and which, when administered to an animal in an effective manner, is capable of protecting that animal from disease caused by a parasitic helminth.

A preferred method to identify a compound capable of inhibiting parasitic helminth DiAg2 activity includes contacting an isolated parasitic helminth DiAg2 protein having an amino acid sequence selected from the group consisting of SEQ ID NO:1, SEQ ID NO:2, SEQ ID NO:4, SEQ ID NO:7, SEQ ID NO:12, SEQ ID NO:17, and/or SEQ ID NO:22 with a putative inhibitory compound under conditions in which, in the absence of said compound, said protein has DiAg2 activity; and determining if said putative inhibitory compound inhibits said activity. An additional step of identifying a compound capable of inhibiting parasitic helminth DiAg2 activity includes contacting an isolated host animal DiAg2 protein with the putative parasitic helminth DiAg2 inhibitory compound under conditions in which, in the absence of said compound, said host animal DiAg2 protein has DiAg2 activity; and determining if said putative inhibitory compound inhibits the host animal DiAg2 activity. A preferred inhibitor inhibits parasitic helminth DiAg2 activity but does not inhibit host DiAg2 activity.

Another embodiment of the present invention is a method to identify a compound capable of inhibiting DiAg2 function of a parasitic helminth. Such a method includes the steps of: (a) identifying a putative compound capable of binding to and/or inhibiting the identified protein binding or regulatory activity of the isolated DiAg2 protein; (b) contacting *D. immitis* L3 larvae with the putative inhibitory compound under conditions in which, in the absence of the compound, the larvae are able to molt to the L4 stage; and (c) determining if the putative compound inhibits molting. Putative inhibitory compounds to screen include small or large organic or inorganic molecules, antibodies (including mimetopes thereof), and ligand analogs. Such compounds are also screened to identify those that are substantially not toxic in host animals.

Inhibitors of DiAg2 function identified by such a method can be tested for their ability to block development and/or migration of parasitic helminths, and particularly of *D. immitis* in vivo. Preferred DiAg2 proteins to inhibit are those produced by parasitic helminths as disclosed herein. A preferred inhibitor of the present invention is capable of protecting an animal from disease caused by parasitic helminths. Compositions comprising inhibitors of DiAg2 function can be administered to animals in an effective manner to protect animals from disease caused by parasitic helminths. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can specifically detect all phases of the parasite's life cycle. Methods to use such diagnostic reagents to diagnose parasitic helminth infection are well known to those skilled in the art, including, for example methods disclosed in PCT Publication No. WO 98/12563, published on Mar. 26, 1998, which is incorporated herein by reference in its entirety. Suitable and preferred parasitic helminths to detect are those to which therapeutic compositions of the present invention are targeted. Preferred parasitic helminths to detect using diagnostic reagents of the present invention are *D. immitis, B. malayi, B. pahangi*, and *O. volvulus.*

The following examples are provided for the purposes of illustration and are not intended to limit the scope of the present invention.

EXAMPLES

Example 1

This example describes the amino acid sequence analysis of a novel 39 kD protein (hereafter referred to as DiAg2) from *Dirofilaria immitis* which reacts with sera from immune dogs.

Internal and N-terminal amino acid sequence of a *D. immitis* DiAg2 protein was obtained as follows. Extracts of adult female *D. immitis* and L4 larvae were separately prepared as described in PCT publication WO 92/13560. A native DiAg2 protein was separated from adult female *D. immitis* extracts and L4 extracts by two dimensional SDS- PAGE as follows. A first dimension separation was obtained by an isoelectric focusing polyacrylamide gel using a non-equilibrium pH gradient containing ampholines of pI 5–8 (available from Pharmacia Biotech, Uppsala, Sweden). A second dimension separation was run on an 8% Tris-glycine gel; the resulting protein spots were transferred to PVDF membranes, and the spot corresponding to D. immitis DiAg2 was identified by 2D immunoblots developed differentially with serum pools from either dogs infected with D. immitis or dogs immune to infection. Twenty-four spots from adult extracts and 24 spots from L4 larvae that reacted strongly with immune sera were separately pooled and used for N-terminal sequence analysis using an automated protein sequencer (ABI437A, available from Applied Biosystems, Inc., Foster City, Calif.). A partial N-terminal amino acid sequence of about 29 amino acids was determined from both L4 larvae and adult females, and is represented herein as SEQ ID NO:1:

KEGKAPHFPQQQVARQNDDDGGTTCCIHR

A homology search of a non-redundant protein sequence database was performed on this amino acid sequence through the National Center for Biotechnology Information (NCBI) (National Library of Medicine, National Institute of Health, Baltimore, Md.) using the BLAST network. This database includes SwissProt+PIR+SPupdate+GenPept+GPUpdate+PDB databases. The search was performed using SEQ ID NO:1 and showed significant homology to Caenorhabditis elegans gene and protein products. The highest scoring match of the homology search at the amino acid level was GenBank™ accession number U39667, a Caenorabditis elegans protein encoded by cosmid clone C18A11, with which SEQ ID NO:1 showed about 94% identity to nucleotides 319 through 336. SEQ ID NO:1 also showed a near sequence identity to residues 3 to 20 of the C. elegans 35.4 kD 2D-PAGE protein spot sequence (GenBank accession number Q18066). When a search was performed using the TBLASTN program and the dbest (EST) database of the BLAST network, the highest scoring match of the homology search at the amino acid level was to a protein encoded by GenBank™ accession number AA283513 (a EST sequence) representing a Brugia malayi cDNA clone, with which SEQ ID NO:1 showed about 94% identity to residues 104 to 157.

Internal amino acid sequence analysis was conducted using excised protein spots prepared by 2-dimensional gels as described above. Forty-eight spots from adult female extracts were pooled and subjected to trypsin digestion in the gel. The digested protein sample was then separated using high pressure liquid chromatography (HPLC). Digested proteins were sequenced as described above. A partial internal amino acid sequence of about 17 amino acids was determined and is represented herein as SEQ ID NO:2:

LTGFSAPTFVEKPQISS

A homology search of a non-redundant protein sequence database was performed on SEQ ID NO:2 through the NCBI using the BLAST network as described above. The highest scoring match of the homology search at the amino acid level was GenBank™ accession number U39667, a Caenorabditis elegans protein encoded by cosmnid clone C18A11 with which SEQ ID NO:2 showed about 94% identity to residues 416 to 432. SEQ ID NO:2 also showed a near sequence identity to residues 100 to 116 of the C. elegans 35.4 kD 2D-PAGE protein spot sequence (GenBank accession number Q18066). When a search was performed using the TBLASTN program and the dbest (EST) database of the BLAST network, the highest scoring match of the homology search at the amino acid level was to a protein encoded by GenBank™ accession number AA283513 (a EST sequence) representing a Brugia malayi cDNA clone with which SEQ ID NO:2 showed 100% identity to residues 395 to 445.

Example 2

This example describes the isolation and sequencing of a nucleic acid molecule encoding a partial D. immitis DiAg2 protein sequence.

Initially, primers were designed based upon C. elegans cosmid clone C18A11 nucleic acid sequence in an attempt to isolate a D. immitis DiAg2 nucleic acid molecule from a D. immitis cDNA library, however, these attempts were unsuccessful. Primers based upon N-terminal and internal amino acid sequence isolated as described in Example 1 were successfully used to isolate a D. immitis DiAg2 nucleic acid molecule as follows. A D. immitis DiAg2 nucleic acid molecule of about 332 nucleotides, denoted $nDiAg2_{332}$, was amplified by polymerase chain reaction (PCR) using D. immitis adult female first strand cDNA as the template, as follows. D. immitis adult female first strand cDNA was prepared from 5 µg of total RNA purified using Tri Reagent®, available from Molecular Research, Inc., Cincinnati, Ohio, according to the manufacturer's instructions and reverse transcribed using a Ready-To-Go™ T-primed first strand synthesis kit, available from Pharmacia, according to the manufacturer's instructions. Degenerate sense primers, having the nucleic acid sequence 5' GGN AAR GCN CCN CAY TTY CCN CAR CA 3', denoted herein as SEQ ID NO:26, encoding amino acid residues 3 through 11 of SEQ ID NO:1, and anti-sense primers, having the nucleic acid sequence 5' AT YTG NGG YTT YTC NAC RAA NGT NGG NGC NSW RAA NCC NGT NA 3', denoted herein as SEQ ID NO:27, encoding amino acid residues 1 through 15 of SEQ ID NO:2 were used to produce a PCR product under the following reaction conditions: 16.375 µl water, 2.5 µl of 10× AmpliTaq buffer with $MgCl_2$, 0.5 µl of 10 mM dNTP's, 0.5 µl of template DNA, 0.5 µl of each primer, and 0.125 µl of AmpliTaq polymerase, available from Perkin-Elmer; using the following PCR cycles, (1) 95° C. for 3 minutes, (2) 35 cycles of (a) 95° C. for 15 seconds, (b) 50° C. for 15 seconds and (c) 72° C. for 90 seconds, (3) 72° C. for 5 minutes, referred to herein as "standard PCR conditions".

The PCR product was separated on a 1% agarose gel at 60 volts for 2 hours and the band of interest was excised and the DNA was purified using a QIA Quick™ kit (available from Qiagen, Chatsworth, Calif.) according to the manufacturer's instructions. The purified DNA was then cloned into TA cloning vector (available from Invitrogen, San Diego, Calif.) according to the manufacturer's instructions and submitted for automated sequence analysis. Sequence analysis revealed a 332-nucleotide nucleic acid molecule, denoted herein as $nDiAg2_{332}$, having a coding strand designated SEQ ID NO:3 and a complementary strand designated SEQ ID NO:5.

Translation of SEQ ID NO:3 yields a protein of about 110 amino acids, denoted $PDiAg2_{110}$, the amino acid sequence of which is designated SEQ ID NO:4, assuming a first codon spanning nucleotides 1 through 3 and a last codon spanning nucleotides 328 through 330 of SEQ ID NO:3.

Example 3

This example describes the isolation of the 3' end of a DiAg2 cDNA from adult female D. immitis by 3' RACE-PCR.

Sequence encoding a partial sequence corresponding to the 3' region of the DiAg2 cDNA was obtained by 3' Rapid Amplification of cDNA Ends (RACE-PCR) using a Marathon™ cDNA amplification kit (available from Clontech, Palo Alto, Calif.) according to the manufacturer's instructions. PCR amplification was performed using first strand adult female *D. immitis* cDNA prepared as described in Example 2 as the template using a sense primer having nucleic acid sequence 5' GGA AAG GGG AAT GCC AAT TTC AAT TTC AAT CTC AAA CTC ACA GGC TTC TGG 3', designated SEQ ID NO:28, which corresponds to nucleotides 1 through 51 of SEQ ID NO:3, and an antisense RACE-adapter primer AP1, having a nucleic acid sequence 5' CCA TCC TAA TAC GAC TCA CTA TAG GGA 3', designated SEQ ID NO:29, (available from Clontech) according to the manufacturer's protocol, under the following conditions 16.5 $\mu$l water, 2.5 $\mu$l of template DNA, 0.5 $\mu$l of Advantageam DNTP mix, 2.5 $\mu$l of Advantage™ buffer, 0.5 $\mu$l of each primer, and 0.5 $\mu$l of 50× of Advantage™ Klen Taq polymerase mix, all available from Clontech; using the following PCR cycles, (1) 94° C. for 1 minute, (2) 3 cycles of (a) 94° C. for 15 seconds, (b) 60° C. for 15 seconds and (c) 68° C. for 4 minutes, (3) 68° C. for 5 minutes.

The resulting PCR product, containing a 775 nucleotide fragment, was ligated into pCR®2.1 vector (Invitrogen, San Diego, Calif.) as described in the manufacturer's protocol and sequenced by the dideoxy chain termination method using an automated sequencer (model 377, Applied Biosystems, Forster City, Calif.). Sequence analysis revealed a 775-nucleotide nucleic acid molecule, denoted herein as $nDiAg2_{775}$, having a coding strand designated SEQ ID NO:6 and a complementary strand designated SEQ ID NO:8.

Translation of SEQ ID NO:6 yields a protein of about 232 amino acids, assuming a first codon spanning nucleotides 1 through 3 and a stop codon spanning nucleotides 697 through 699 of SEQ ID NO:6, denoted $PDiAg2_{232}$, and having an amino acid sequence designated SEQ ID NO:7. The nucleic acid molecule encoding $PDiAg2_{232}$, referred to herein as $nDiAg2_{699}$, has a coding sequence designated SEQ ID NO:9 (the coding strand) and a complementary strand designated SEQ ID NO:10.

Example 4

This example describes the isolation of the 5' end of a DiAg2 cDNA from adult female *D. immitis*.

A *D. immitis* DiAg2 molecule was PCR amplified using *D. immitis* adult female first strand cDNA prepared as described in Example 2 as the template using a primer corresponding to a nematode splice leader (SL) as follows. Sense primer SL, having a nucleotide sequence, 5' GGT TTA ATT ACC CAA GTT TGA G 3', designated SEQ ID NO:30, and an antisense primer 5' CCA GAA GCC TGT GAG TTT GAG ATT GAA ATT GGC ATT CCC CTT TCC 3', designated SEQ ID NO:31, were used to PCR amplify a 376-nucleotide product under standard PCR conditions, denoted herein as $nDiAg_{376}$.

The resulting PCR product was purified as described above and cloned into TA cloning vector (available from Invitrogen) and sequenced using an automated DNA sequencer. Sequence analysis revealed an about 376 nucleotide fragment, denoted herein as $nDiAg2_{376}$ having a coding sequence designated SEQ ID NO: 11, and a complementary sequence designated SEQ ID NO: 13 which had SL sequence at its 5' end. Translation of SEQ ID NO:11 yields a protein of about 104 amino acids, assuming a first codon spanning nucleotides 65 through 67 and a last codon spanning nucleotides 374 through 376 of SEQ ID NO:11, denoted $PDiAg2_{104}$ having an amino acid sequence designated SEQ ID NO:12. The coding region of $PDiAg2_{104}$ is referred to herein as $nDiAg2_{312}$, having a coding strand designated SEQ ID NO:14 and a complementary strand designated SEQ ID NO: 15.

The sequences of $nDiAg2_{376}$, $nDiAg2_{332}$ and $nDiAg_{775}$, were aligned to construct a composite DiAg2 sequence representing a cDNA encoding a full-length *D. immitis* DiAg2 protein. The nucleic acid molecule represented by this sequence, denoted $nDiAg2_{1106}$ includes both the nematode splice leader sequence at the 5' end of the molecule, and poly(A)+ sequence at the 3' end of the molecule. The nucleic acid sequence of the coding and complementary strands of $nDiAg2_{1106}$ are herein represented by SEQ ID NO:16 and SEQ ID NO:18, respectively. Translation of $nDiAg2_{1106}$ yields an approximately 321 amino acid protein herein denoted as $PDiAg2_{321}$, assuming an initiation codon spanning nucleotides 65 through 67 and a stop codon spanning nucleotides 1028 through 1030 of SEQ ID NO:16, the amino acid sequence of which is presented in SEQ ID NO:17. The nucleic acid molecule encoding $PDiAg2_{321}$, denoted $nDiAg2_{963}$, has a coding sequence designated SEQ ID NO:19 and a complementary sequence designated SEQ ID NO: 20.

Homology searches were performed on SEQ ID NO:16 and SEQ ID NO:17, through the NCBI using the BLAST network as described above. The highest scoring match of the homology search at the amino acid level was GenBank™ accession number U39667, a *Caenorabditis elegans* protein encoded by cosmid clone C18A11 and the highest scoring match at the nucleic acid level was to *Caenorabditis elegans* cosmid clone C18A11. The highest scoring matches were aligned using the PC/GENE DNA Sequence Analysis System, available from Intelligenetics, Inc., Mountainview, Calif., using default parameters, which indicated about 68% identity at the nucleic acid level and about 78% identity at the amino acid level.

Example 5

This Example describes the isolation of a nucleic acid molecule encoding a full-length DiAg2 protein from *D. immitis* cDNA and production of a recombinant cell comprising a nucleic acid molecule encoding a full-length DiAg2 protein from *D. immitis*.

A *D. immitis* DiAg2 molecule encoding a full-length DiAg2 protein was PCR amplified from adult female first strand cDNA prepared as described above using sense primer DiAg2-XhoI, having nucleotide sequence 5' CCG AGC TCG AGA ATG CCG GAG GGT AAA GCA CCT CAT 3', designated SEQ ID NO:32 and having a XhoI site indicated in bold, and antisense primer DiAg2-PstI, having a nucleotide sequence 5' CCA GCT GCA GAT CAC GCT TCG CTA GCA TCA TCT GC 3', designated SEQ ID NO:33 and having a PstI site indicated in bold, under the following PCR conditions.

The resulting PCR product was purified as described above and cloned into TA cloning vector (available from Invitrogen) and sequenced using an automated DNA sequencer. Sequence analysis revealed a 989-nucleotide product, denoted $nDiAg2_{989}$, having a coding sequence designated SEQ ID NO:21 and a complementary sequence denoted SEQ ID NO:23. Translation of SEQ ID NO:21 yields a protein of about 321 amino acids, denoted $PDiAg2_{321}$, assuming an initiation codon spanning nucleotides 13 through 15 and a stop codon spanning nucleotides 976 through 978 of SEQ ID NO:21, the amino acid sequence of which is presented in SEQ ID NO:22. The nucleic acid molecule encoding PDiAg2$_{321}$, denoted nDiAg2$_{963}$, has a coding sequence designated SEQ ID NO:19 and a complementary sequence designated SEQ ID NO: 20. The amino acid sequence of PDiAg2$_{321}$, i.e., SEQ ID NO: 17, (also represented herein as SEQ ID NO:22), predicts that PDiAg2$_{321}$ has an estimated molecular weight of about 35.5 kDa and an estimated pI of about 4.65.

Recombinant molecule pHis-nDiAg2$_{966}$, containing a *D. immitis* DiAg2 nucleic acid molecule operatively linked to araBAD transcription control sequences and to a fusion sequence encoding a poly-histidine segment of 6 histidine residues, was produced in the following manner. An about 966 nucleotide DNA fragment corresponding to nucleotides 1 through 966 of SEQ ID NO:19, denoted herein as nDiAg2$_{966}$, was produced by digesting molecule nDiAg2$_{989}$, produced by PCR amplification as described in Example 2, with XhoI and PstI restriction endonucleases, gel purifying the resulting fragment and directionally subcloning it into expression vector pBAD (available from Invitrogen, San Diego, Calif.) that had been digested with XhoI and PstI and gel purified.

Recombinant molecule pHis-nDiAg2$_{966}$ was transformed into *E. coli* to form recombinant cell *E. coli*:pHis-nDiAg2$_{966}$ using standard techniques as disclosed in Sambrook et al., ibid.

Example 6

This example describes the production of a *D. immitis* DiAg2 protein of the present invention in a prokaryotic cell and immunoblot analysis of the expressed protein.

Recombinant cell *E. coli*:pHis-nDiAg2$_{966}$, produced as described in Example 5, was cultured in shake-flasks containing an enriched bacterial growth medium containing 0.1 mg/ml ampicillin at about 37° C. When the cells reached an OD$_{600}$ of about 0.5, expression of *E. coli* pHis-nDiAg2$_{966}$ was induced by addition of about 0.5 mM IPTG, and the cells were cultured for about 3 hr at about 37° C. Protein production was monitored by SDS-PAGE of recombinant cell lysates, followed by Coomassie blue staining. Recombinant cell *E. coli*:pHis-nDiAg2$_{966}$ produced a fusion protein, denoted herein as pHis-PDiAg2$_{321}$, that migrated with an apparent molecular weight of about 43 kDa.

Immunoblot analysis of recombinant cell *E. coli*:pHis-nDiAg2$_{966}$ lysates indicated that the about 43-kDa protein was able to bind to a T7 Tag® monoclonal antibody (available from Novagen, Inc., Madison, Wis.) directed against the fusion portion of the recombinant pHis-PDiAg2$_{321}$ fusion protein.

The pHis-PDiAg2$_{321}$ histidine fusion protein was separated from *E. coli* proteins by cobalt chelation chromatography with an imidazole gradient elution. Immunoblot analysis of the *E. coli*:pHis-PDiAg2$_{966}$ lysates, column eluate and column void volume indicated that the pHis-PDiAg2$_{321}$ 43-kDa protein isolated using cobalt column chromatography was able to selectively bind to a T7 Tag® monoclonal antibody (available from Novagen). The fusion peptide expressed in araBAD contributes approximately 4 kDa to the recombinant protein, and thus nDiAg2$_{966}$ encodes a protein of approximately 39 kDa.

Example 7

This Example discloses the purification of a DiAg2 fusion protein of the present invention from total cell lysates and production of an anti-pHis-PDiAg2$_{321}$ antibody.

DiAg2 fusion protein pHis-PDiAg2$_{321}$, produced as described in Example 6, was separated from *E. coli* proteins by Talonrh Metal Affinity Resin Chromatography (available from CLONTECH Laboratories, Inc., Palo Alto, Calif.) according to manufacturer's instructions. The DiAg2 fusion protein was eluted using an imidazole gradient, pooled and dialyzed against 1× phosphate buffered saline (PBS) to produce cobalt column-purified pHis-PDiAg2$_{321}$. The dialyzed protein was concentrated using a 10K molecular weight cut off Centrifugal Ultra-free® concentrator (available from Millipore Corporation, Bedford, Mass.). The protein content of the fusion protein was determined by using a MicroBCA™ Protein Assay (available from Pierce, Rockford, Ill.). The purified protein was tested for its purity by SDS PAGE and immunoblot analysis as described in Example 6.

Anti-pHis-PDiAg2$_{321}$ (anti-DiAg2) antisera was produced as follows: A rabbit was immunized subcutaneously, first with approximately 75 μg of purified pHis-PDiAg2$_{321}$ protein with complete Freund's Adjuvant, and then with three subsequent immunizations of the same dose mixed in Incomplete Freund's Adjuvant, each available from Sigma, St. Louis, Mo. Bleeding and immunization were performed at alternate weeks. Sera were separated and stored at −70° C. until use.

Immunoglobulin G (IgG) fraction (DiAg2-IgG) from anti-DiAg2 antisera was collected by 50% ammonium sulfate precipitation. Ammonium ions were removed by extensive dialysis in 0.1 M PBS, pH 7.2. The IgG content was determined by measuring absorbence at OD$_{280}$ versus a blank PBS control. The DiAg2-IgG had an OD$_{490}$ of 4.0 at a serum dilution 1:6400 as determined by ELISA.

Example 8

This Example describes the identification of native *D. immitis* DiAg2 by immunoblot analysis. Rabbit anti-DiAg2-IgG produced as described in Example 7, was used to identify a native *D. immitis* DiAg2 protein in *D. immitis* extract as follows.

Crude extracts of *D. immitis* larvae, adult male and female worms, and larval cuticles were separated by 12% Tris-glycine SDS-PAGE for 1 hour at 200 volts and 5 μg protein per lane then transferred to a nitrocellulose membrane by standard methods. Following transfer, the membrane was blocked in 5% nonfat dry milk for 1 hr at 37° C. then incubated for 1 hour at room temperature in a 1:500 dilution of rabbit anti-DiAg2-IgG in Tris buffered saline. The blot was then washed, and antibody binding was resolved using a peroxidase-labeled rabbit IgG secondary antibody and the substrate NBT/BCIP (available from Sigma). Immunoblot analysis of *D. immitis* adult male, female and larval extracts from L3, L4 and microfilaria larvae identified a native 39 kDa protein. A 39 kDa was also identified in extracts prepared from L3 larval cuticles.

Example 9

This Example describes the identification of 39 kDa *D. immitis* DiAg2 protein by immuno-precipitation using rabbit anti-DiAg2-IgG and detection of immunoprecipitated protein by immune, and infected dog sera A Protein-G Immunoprecipitation Kit, available from Pierce Chemical Co. Rockford, Ill., was used for immuno-precipitation of a native DiAg2 protein as follows. Protein-G beads were first blocked with protein extracts from adult female *D. immitis*. For immune-complex preparation, 1 mg of adult female protein extract was mixed with 250 μg of rabbit anti-DiAg2-IgG and incubated at 4° C. for 1 hr and 150 µl of previously blocked protein-G beads were added and incubated overnight. The beads were then washed in wash buffer according to the manufacturer's protocol then resuspended in SDS-PAGE sample buffer for further analysis.

The immunoprecipitated proteins were separated on 8% SDS-PAGE trough gel and transferred to nitrocellulose membranes. After transfer, the membrane was blocked in 5% nonfat dry milk for 1 hr at 37° C. The membrane was cut into strips and incubated separately with various sera including immune dog sera, infected dog sera, normal dog sera, and rabbit anti-DiAg2-IgG as a positive control. After 2 hr incubation at room temperature, the strips were washed, and antibody binding resolved using either a peroxidase-labeled dog or rabbit IgG secondary antibody and the substrate NBT/BCIP (available from Sigma). The immunoprecipitated native DiAg2 which migrated at about 39 kDa, reacted with the immune dog sera and rabbit anti-DiAg2-IgG. Recombinant protein DiAg2$_{321}$, prepared as described in Example 7, was also separated by SDS-PAGE as described above and shown to react with immune dog serum and rabbit anti-DiAg2-IgG. The infected dog sera reacted weakly to native and recombinant DiAg2 proteins and rabbit anti-DiAg2-IgG. Normal dog sera did not react with any strip or control tested.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein selected from the group consisting of: (a) a protein comprising an amino acid sequence selected from the group consisting of SEQ ID NO:4, SEQ ID NO:7, SEQ ID NO:12, and SEQ ID NO:22; and (b) a protein comprising an at least 30 consecutive amino acid portion identical in sequence to a 30 consecutive amino acid portion of a sequence selected from the group consisting of SEQ ID NO:4, SEQ ID NO:7, SEQ ID NO:12, and SEQ ID NO:22.

2. The protein of claim 1, wherein said protein is encoded by a nucleic acid molecule having a nucleic acid sequence selected from the group consisting of SEQ ID NO:3, SEQ ID NO:6, SEQ ID NO:9, SEQ ID NO:11, SEQ ID NO:14, SEQ ID NO:16, SEQ ID NO:19 and SEQ ID NO:21.

3. The protein of claim 1, wherein said protein comprises an amino acid sequence selected from the group consisting of SEQ ID NO:4, SEQ ID NO:7, SEQ ID NO:12, and SEQ ID NO:22.

4. An isolated protein comprising a filariid nematode protein that is at least 85% identical to an amino acid sequence selected from the group consisting of SEQ ID NO:4, SEQ ID NO:7, SEQ ID NO:12, and SEQ ID NO:22.

5. The protein of claim 4, wherein said protein is encoded by a nucleic acid molecule having a nucleic acid sequence selected from the group consisting of SEQ ID NO:3, SEQ ID NO:6, SEQ ID NO:9, SEQ ID NO:11, SEQ ID NO:14, SEQ ID NO:16, SEQ ID NO:19 and SEQ ID NO:21.

6. A composition comprising an excipient and a compound selected from the group consisting of: (a) a protein comprising an amino acid sequence selected from the group consisting of SEQ ID NO:4, SEQ ID NO:7, SEQ ID NO:12, and SEQ ID NO:22; and (b) a protein comprising an at least 30 consecutive amino acid portion identical in sequence to a 30 consecutive amino acid portion of a sequence selected from the group consisting of SEQ ID NO:4, SEQ ID NO:7, SEQ ID NO:12, and SEQ ID NO:22.

7. The composition of claim 6, wherein said protein is encoded by a nucleic acid molecule having a nucleic acid sequence selected from the group consisting of SEQ ID NO:3, SEQ ID NO:6, SEQ ID NO:9, SEQ ID NO:11, SEQ ID NO:14, SEQ ID NO:16, SEQ ID NO:19 and SEQ ID NO:21.

8. The composition of claim 6, wherein said protein comprises an amino acid sequence selected from the group consisting of SEQ ID NO:4, SEQ ID NO:7, SEQ ID NO:12, and SEQ ID NO:22.

9. The composition of claim 6, wherein said composition further comprises a component selected from the group consisting of an adjuvant and a carrier.

10. A method to identify a compound capable of inhibiting filariid DiAg2 activity, said method comprising:

(1) contacting an isolated protein selected from the group consisting of
 (a) a protein comprising an amino acid sequence selected from the group consisting of SEQ ID NO:4, SEQ ID NO:7, SEQ ID NO:12, and SEQ ID NO:22, and
 (b) a protein comprising an at least 30 consecutive amino acid portion identical in sequence to a 30 consecutive amino acid portion of a sequence selected from the group consisting of SEQ ID NO:4, SEQ ID NO:7, SEQ ID NO:12, and SEQ ID NO:22
with a putative inhibitory compound under conditions in which, in the absence of said compound, said protein has DiAg2 activity; and (2) determining if said putative inhibitory compound inhibits said activity.

11. The method of claim 10, wherein said protein is encoded by a nucleic acid molecule having a nucleic acid sequence selected from the group consisting of SEQ ID NO:3.

12. The method of claim 10, wherein said protein comprises an amino acid sequence selected from the group consisting of SEQ ID NO:4, SEQ ID NO:7, SEQ ID NO:12, and SEQ ID NO:22.

* * * * *